United States Patent
Iwama et al.

(10) Patent No.: US 7,189,790 B2
(45) Date of Patent: Mar. 13, 2007

(54) CATALYST COMPONENT FOR OLEFIN POLYMERIZATION, CATALYST FOR α-OLEFIN POLYMERIZATION AND PROCESS FOR THE PRODUCTION OF α-OLEFIN POLYMER

(75) Inventors: Naoshi Iwama, Mie (JP); Takao Tayano, Mie (JP); Hisashi Ohtaki, Kanagawa (JP)

(73) Assignee: Japan Polypropylene Corporation, Tokyo (JP)

( * ) Notice: Subject to any disclaimer, the term of this patent is extended or adjusted under 35 U.S.C. 154(b) by 174 days.

(21) Appl. No.: 10/940,769

(22) Filed: Sep. 15, 2004

(65) Prior Publication Data
US 2005/0070426 A1    Mar. 31, 2005

(30) Foreign Application Priority Data
Sep. 30, 2003  (JP) .............................. 2003-340108

(51) Int. Cl.
*C08F 4/639*   (2006.01)
*C08F 4/64*   (2006.01)
(52) U.S. Cl. ...................... 526/160; 526/134; 526/165; 526/943; 502/103; 502/152
(58) Field of Classification Search ................... 526/16, 526/165, 943; 502/152, 103
See application file for complete search history.

(56) References Cited

FOREIGN PATENT DOCUMENTS

| JP | 6-100579 | 4/1994 |
| JP | 7-286005 | 10/1995 |
| JP | 10-226712 | 8/1998 |
| JP | 11-189617 | 7/1999 |
| JP | 2000-95791 | 4/2000 |
| JP | 2001-48894 | 2/2001 |
| JP | 2002-12596 | 1/2002 |
| WO | WO 02/02576 A1 | 1/2002 |

OTHER PUBLICATIONS

Database CA 'Online!, Iwama Tadashi, et al., "Transition metal compounds, catalysts containing them, and manufacture of .alpha.-olefin polymers with high stereoregularity", Chemical Abstracts Service, Database Accession No. 2000:218579, XP-002314202, JP 2000-095791, Apr. 4, 2000, pp. 1-5.

Database CA 'Online!, Masami Kashimoto, et al, "Preparation of alpha-olefin polymers with high melting point, catalysts therefor and metaliocene transition metal complexes therein", Chemical Abstracts Service, Database Accession No. 2003:805785, XP-002314387, JP 2003-292518, Oct. 15, 2003, pp. 1-11.

*Primary Examiner*—Caixia Lu
(74) *Attorney, Agent, or Firm*—Oblon, Spivak, McClelland, Maier & Neustadt, P.C.

(57) ABSTRACT

To develop a catalyst component for olefin polymerization, a metallocene catalyst for olefin polymerization and a process for the production of an olefin polymer capable of producing an olefin polymer having a high molecular weight and a high melting point which can be extruded or injection-molded in a high yield and a novel transition metal compound to be used in these catalyst components a catalyst component for olefin polymerization is made of a transition metal compound represented by formula (I) shown below; a metallocene catalyst for olefin polymerization comprises the catalyst component for olefin polymerization; and a process for the production of an olefin polymer is performed in the presence of the metallocene catalyst for olefin polymerization:

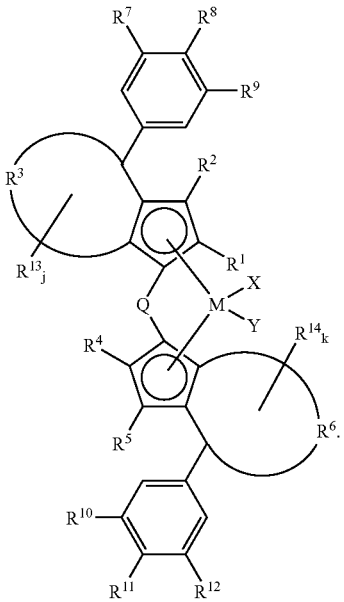

12 Claims, No Drawings

CATALYST COMPONENT FOR OLEFIN POLYMERIZATION, CATALYST FOR α-OLEFIN POLYMERIZATION AND PROCESS FOR THE PRODUCTION OF α-OLEFIN POLYMER

BACKGROUND OF THE INVENTION

1. Field of the Invention

The present invention relates to a novel catalyst component for olefin polymerization, a catalyst for α-olefin and a process for the production of an α-olefin polymer using the catalyst. More particularly, the present invention relates to a high activity metallocene catalyst for α-olefin polymerization comprising a novel catalyst component for olefin polymerization capable of producing an α-olefin polymer having a high molecular weight and a high melting point, a process for the production of an α-olefin polymer using the metallocene catalyst for α-olefin polymerization and a novel transition metal compound constituting a catalyst component for olefin polymerization.

2. Background Art

It has been keenly desired that industrially very important polyolefins have further improvement of physical properties such as melting point, stereoregularity and rigidity of the polymer. It has been also desired that the particulate polymers have good properties from the standpoint of safety in production operation. One of specific technical means meeting these requirements for enhancement is using a metallocene catalyst.

As one of representative techniques, in a bridged metallocene catalyst which has an indenyl skeleton or azulenyl skeleton comprising a conjugated 5-membered ring condensed to other conjugated ring, the stereospecificity of substituents at the 4-position on the indenyl skeleton or azulenyl skeleton is noted and there is reported that the characterization of the kind of the substituents makes it possible to enhance the polymerization activity and molecular weight, further the melting point of the crystalline polyolefin (Patent References 1 and 2).

As can be seen in Patent Reference 2, it was found that when the substituent at the 4-position of the ring is an aromatic ring such as phenyl group, a remarkable enhancement of polymer properties such as the stereoregularity and molecular weight distribution can be realized. Some methods for further introducing substituents on the aromatic ring to further enhance the catalyst properties have been reported (see Patent References 3 to 7).

Patent Reference 3 discloses a catalyst complex comprising an indenyl skeleton having an aryl group substituted by a hydrocarbon group or halogen atom at the 4-position thereof. It is also disclosed that a high catalytic activity is obtained and that an olefin polymer having an enhanced stereoregularity. Patent Reference 4 discloses a catalyst complex comprising an indenyl skeleton having a phenyl group substituted by a plurality of hydrocarbon groups or silyl groups at the 4-position thereof. It is also disclosed that an olefin polymer having an enhanced melting point is obtained.

Patent Reference 5 discloses a catalyst complex comprising an azulenyl skeleton having, at the 4-position thereof, a phenyl group substituted by a phenyl group at the 4-position of the phenyl group (para-position) (biphenylyl group as a whole) and a hydrocarbon group or halogen atom at the 2- or 6-position of the biphenylyl group. It is also disclosed that an olefin polymer having an enhanced stereoregularity, melting point and molecular weight is obtained. Patent Reference 6 discloses a catalyst complex comprising an azulenyl skeleton having a phenyl group to which other carbon rings are condensed at the 4-position thereof. It is also disclosed that an olefin polymer having an enhanced stereoregularity, melting point and molecular weight is obtained. Patent Reference 7 discloses a catalyst complex comprising an azulenyl skeleton having, at the 4-position thereof, a phenyl group substituted by a silyl group at the 4-position of the phenyl group. It is also disclosed that an olefin polymer having an enhanced stereoregularity, melting point and molecular weight is obtained.

Further, Patent Reference 8 discloses a catalyst complex comprising two azulenyl ligands bridged by an alkylsilylene group, the alkylsilylene group having an alkyl moiety which forms a annular structure with a silicon atom. However, the disclosure of substituents at the 4-position of azulenyl skeleton is limited to some examples.

(Patent Reference 1)
  JP-A-6-100579 (abstract)

(Patent Reference 2)
  JP-A-10-226712 (abstract; paragraph (0005), (0028))

(Patent Reference 3)
  JP-A-7-286005 (abstract; claim 1)

(Patent Reference 4)
  WO02/02576 (p. 79, 80, 86, 90, 91)

(Patent Reference 5)
  JP-A-2000-95791 (abstract; claims 1, 3, 4; paragraph (0055))

(Patent Reference 6)
  JP-A-2001-48894 (abstract; claim 1)

(Patent Reference 7)
  JP-A-2002-12596 (abstract; claim 3)

(Patent Reference 8)
  JP-A-11-189617 (abstract; claims; paragraph (0052) to (0059)).

SUMMARY OF THE INVENTION

The inventors made experimental trials aiming at further enhancement of all of catalytic activity of metallocene catalyst, efficiency of production by high temperature polymerization, molecular weight, stereoregularity, melting point, physical properties and granularity of polymer according to the current trend for technical improvement, i.e., selection of the kind of substituents at the 4-position on the indenyl skeleton or azulenyl skeleton. As a result, a novel favorable catalyst structure was found. The present applicant filed this catalyst structure as an invention prior to the present invention (Japanese Patent Application 2002-101390).

The inventors sought a better metallocene complex taking into account these results, and an object of the present invention is to provide the better metallocene complex.

Another object of the present invention is to provide a catalyst for olefin polymerization comprising the aforementioned catalyst component and a process for the production of an olefin polymer using the catalyst. A further object of the present invention is to provide a novel catalyst component which shows little performance deterioration when supported on a carrier to improve process adaptability.

In order to accomplish the aforementioned objects of the invention and solve the aforementioned problems, the inventors made further studies and experiments during which the inventive concept of the aforementioned related art invention was developed. In an experimental search course taking in to account the kind and position of further substituents on the phenyl substituent or combination thereof, a fact was recognized that when a relatively bulky substituent is disposed at the 4-position (para-position) of a phenyl group, the phenyl group being disposed at the 4-position of the azulenyl or indenyl skeleton, and substituents are disposed at both the 3-position and 5-position adjacent to the 4-position of the phenyl group, the resulting catalyst is far more excellent than the catalyst component of the related art inventions. Thus, a novel metallocene complex which is very useful as a catalyst component was discovered. The invention has thus been worked out.

The present invention concerns a novel catalyst component which is characterized by a specificity in steric configuration of substituents. In some detail, a relatively bulky substituent is disposed at the 4-position (para-position) of a phenyl group, the phenyl group being disposed at the 4-position on the indenyl skeleton or azulenyl skeleton. Further, substituents are disposed at both the 3-position and 5-position adjacent to the 4-position of the phenyl group.

The aforementioned metallocene complex comprises a novel transition metal compound having a structure represented by formula (I). The metallocene complex is used as a catalyst component of catalyst for olefin polymerization in the present invention. The metallocene complex is combined with a cocatalyst to form a catalyst for α-olefin polymerization.

Formula (I):

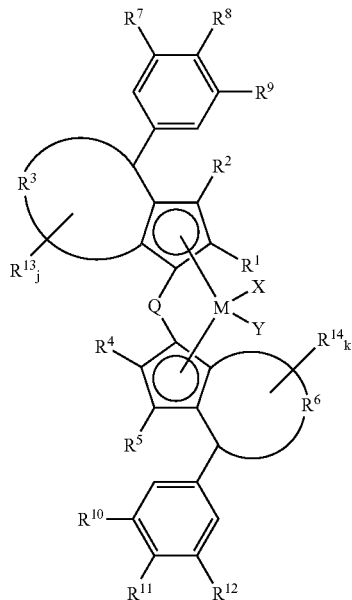

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3, or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, and $R^{13}$ and $R^{14}$ substitute a hydrogen atom in the hydrocarbon group represented by $R^3$ and $R^6$, respectively;

j and k each represent an integer of 0 to 8;

Q represents a bridging group connecting two cyclopentadienyl rings;

X and Y each represent an auxiliary ligand which is σ-covalently bound to M, the auxiliary ligand being capable of reacting with a cocatalyst to develop an olefin-polymerizing capability; and M represents a transition metal belonging to the group IV in the periodic table.

The use of a transition metal compound of the present invention as a catalyst component for olefin polymerization makes it possible to accomplish the objects of obtaining a polyolefin having a high molecular weight, a high melting point and excellent properties which can be extruded or injection-molded in a high yield as described later in the examples. The reason is not necessarily obvious but can be presumed as follows.

When there are bulky substituents disposed on $R^8$ and $R^{11}$ and substituents disposed on $R^7$, $R^9$, $R^{10}$ and $R^{12}$ on the phenyl group at the 4-position of the indenyl skeleton or azulenyl skeleton, the direction of growth of polymer chain and the direction of coordination of monomers can be effectively controlled. The phenyl group substituted at the 4-position of the indenyl skeleton or azulenyl skeleton rotates freely also during the polymerization reaction. In the case of the related art inventions wherein only one of $R^7$ and $R^9$ or $R^{10}$ and $R^{12}$ has substituents (that is, one of $R^7$ and $R^9$ or $R^{10}$ and $R^{12}$ is a hydrogen atom), it is thought that the steric effect is insufficient. On the contrary, in the case of the present invention, wherein both of $R^7$ and $R^9$ or $R^{10}$ and $R^{12}$ have substituents (both of $R^7$ and $R^9$ or $R^{10}$ and $R^{12}$ are not a hydrogen atom), it is thought that the steric effect can be exerted more effectively. As a result, it is presumed that the action of controlling the direction of growth of polymer chain and the direction of coordination of monomers can be enhanced, making it possible to obtain a polymer having an enhanced stereoregularity and hence a higher melting point.

In the present invention, as above-described, a catalyst component for olefin polymerization, comprising a transition metal compound represented by formula (I), constitutes a basic invention (1). The following polymerization catalysts (2) to (4), too, are embodiments of implementation of the invention.

(2) The catalyst component for olefin polymerization as defined in clause (1), wherein the transition metal compound represented by formula (I) has an asymmetrical molecular structure about a plane including M, X and Y.

(3) The catalyst component for olefin polymerization as defined in clause (1), wherein $R^8$ and $R^{11}$ each independently represent a silicon-containing hydrocarbon group having a carbon number of 3 to 10 or a branched aliphatic hydrocarbon group having a carbon number of 3 to 10.

(4) The catalyst component for olefin polymerization as defined in clause (3), wherein $R^7$, $R^9$, $R^{10}$ and $R^{12}$ each are a halogen atom.

The present invention is embodied also by the following polymerization catalysts (5) and (6).

(5) A catalyst for α-olefin polymerization, which comprises:

(A) a transition metal compound represented by formula (I) as defined in clause 1;

(B) a component at least one of an aluminum oxy compound, an ionic compound capable of reacting with the transition metal compound to convert the transition metal compound to a cation, a Lewis acid, and a solid acid; and optionally (C) a particulate carrier.

(6) A catalyst for α-olefin polymerization, which comprises:

(A) a transition metal compound represented by formula (I) as defined in clause 1;

(D) at least one of an ion-exchanging layered compound and an inorganic silicate; and optionally (E) an organic aluminum compound.

The present invention is embodied also by the following polymerization process (7):

(7) A process for producing an α-olefin polymer, which comprises bringing an α-olefin into contact with a catalyst as defined in clause (5) or (6) to polymerize or copolymerize the α-olefin.

The present invention is embodied also by the following transition metal compound (8):

(8) A transition metal compound represented by the formula (I):

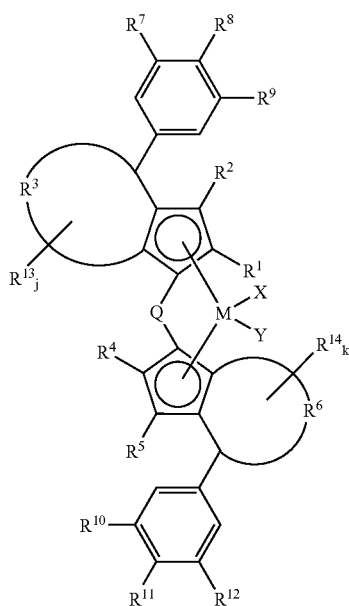

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3, or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, and $R^{13}$ and $R^{14}$ substitute a hydrogen atom in the hydrocarbon group represented by $R^3$ and $R^6$, respectively;

j and k each represent an integer of 0 to 8;

Q represents a bridging group connecting two cyclopentadienyl rings;

X and Y each represent an auxiliary ligand which is ρ-covalently bound to M; and M represents a transition metal belonging to the group IV in the periodic table.

When an olefin is polymerized in the presence of the catalyst component for olefin polymerization and the olefin polymerization catalyst comprising the novel transition metal compound of the present invention, the action of controlling the direction of growth of polymer chain and the direction of coordination of monomers can be enhanced, making it possible to obtain a polyolefin having an enhanced polymer stereoregularity, a high molecular weight, a high melting point and excellent physical properties which can be extruded or injection-molded in a high yield. In particular, the olefin polymerization catalyst made of the transition metal compound (metallocene) of the invention and the ion-exchanging layered compound or inorganic silicate shows a small depression of melting point when supported on a carrier and thus is industrially favorable.

DETAILED DESCRIPTION OF THE INVENTION

The above-described embodiments of the present invention is further described hereinafter as best modes for carrying out the invention.

1. Transition Metal Compound to be Used as a Catalyst Component for Olefin Polymerization 1.-(1) Structure of Transition Metal Compound As described above, the transition metal compound constituting the metallocene complex in the metallocene catalyst of the present invention is a novel transition metal compound represented by formula (I):

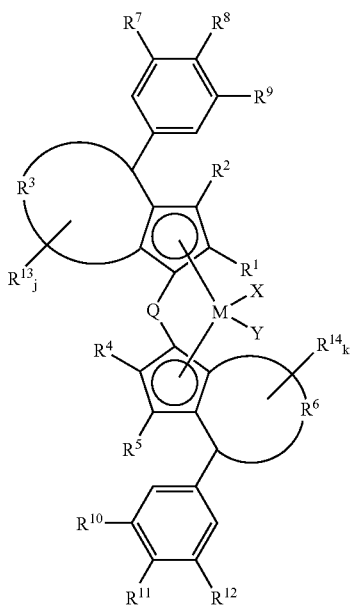

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3, or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, and $R^{13}$ and $R^{14}$ substitute a hydrogen atom in the hydrocarbon group represented by $R^3$ and $R^6$, respectively;

j and k each represent an integer of 0 to 8;

Q represents a bridging group connecting two cyclopentadienyl rings;

X and Y each represent an auxiliary ligand which is σ-covalently bound, the auxiliary ligand being capable of reacting with a cocatalyst to develop an olefin-polymerizing capability; and M represents a transition metal belonging to the group IV in the periodic table.

In the present specification, as the periodic table there is used a short form of the periodic table.

1.-(2) Characteristics of Transition Metal Compound

One of the characteristics of the transition metal compound of the present invention as a ligand of complex is that it has substituents at the specific position on the ligand. The structure of the transition metal compound of the present invention is specific and novel such that the phenyl group at the 4-position of an indenyl skeleton or azulenyl skeleton has a relatively bulky substituent disposed at the 4-position (para) thereof and substituents disposed at both the adjacent 3-position and 5-position thereof.

It is possible that the transition metal compound of the invention should have compounds (a) and compounds (b) in which the ligand of the 5-membered ring having substituents $R^1$, $R^2$ and $R^3$ and the ligand of the 5-membered ring having substituents $R^4$, $R^5$ and $R^6$ are asymmetric and symmetric, respectively, about a plane including M, X and Y from the standpoint of position relative to the connecting group Q.

However, in order to produce an α-olefin polymer having a high molecular weight and a high melting point, it is preferred that the aforementioned compounds (a) which are rac-ansa-metallocene isomers, i.e., compounds in which the two ligands of the 5-membered ring disposed opposed to each other with a plane including M, X and Y interposed therebetween are not mirror images of each other be used from the standpoint of action of controlling the direction of growth of polymer chain and the direction of coordination of monomers.

1.-(3) Substituents on Transition Metal Compound

In formula (I), $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6.

Specific preferred examples of the aforementioned hydrocarbon group having the carbon number of 1 to 6 include alkyl groups such as methyl, ethyl, n-propyl, i-propyl, n-butyl, i-butyl, s-butyl, t-butyl, n-pentyl, n-hexyl, cyclopropyl, cyclopentyl and cyclohexyl; alkenyl groups such as vinyl, propenyl and cyclohexenyl; and phenyl groups.

Specific preferred examples of the aforementioned silicon-containing hydrocarbon group having a carbon number of 1 to 7 include trialkylsilyl groups such as trimethylsilyl, trietylsilyl and t-butyldimethylsilyl; and alkylsilylalkyl groups such as bis(trimethylsilyl) methyl.

Preferred examples of the halogen atom to be incorporated in the aforementioned halogenated hydrocarbon group having a carbon number of 1 to 6 include fluorine atom, chlorine atom, bromine atom and iodine atom. The aforementioned halogenated hydrocarbon group is a compound having a fluorine atom, if the halogen atom is a fluorine atom, substituted on arbitrary positions on the above-described hydrocarbon group.

Specific examples of the aforementioned halogenated hydrocarbon group include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,4-difluorophenyl, 2,5-difluorophenyl, 2,6-difluorophenyl, 3,5-difluorophenyl, 2,4-dichlorophenyl, 2,5-dichlorophenyl, 2,6-dichlorophenyl, 3,5-dichlorophenyl, 2,4,6-trifluorophenyl, 2,4,6-trichlorophenyl, pentafluorophenyl, and pentachlorophenyl.

Preferred among these compounds represented by $R^1$ and $R^4$ is the hydrocarbon group having a carbon number of 1 to 6, particularly the alkyl group having a carbon number of 1 to 6 such as methyl, ethyl, propyl and butyl. Particularly preferred among the compounds represented by $R^2$ and $R^5$ is hydrogen atom.

In formula (I), $R^3$ and $R^6$ each represent a hydrocarbon connecting group which is connected to a cyclopentadienyl ring to form any one of a 5- to 10-membered condensed ring. As shown by the aforementioned formula, one of the characteristics of the present invention is that there is a substituted phenyl group disposed at the 4-position on the ring condensed to the cyclopentadienyl ring (counted with the position of the carbon atom to which the bridging group is connected as 1). As the hydrocarbon connecting groups $R^3$ and $R^6$ there may be used any groups unless such a structural characteristic is lost.

Preferred examples of these connecting groups $R^3$ and $R^6$ include a saturated or unsaturated divalent hydrocarbon connecting group having a carbon number of 2 to 8. Specific examples of the saturated or unsaturated divalent hydrocarbon connecting group having a carbon number of 2 to 8 include divalent saturated hydrocarbon groups such as dimethylene, trimethylene, tetramethylene, pentamethylene and hexamethylene; and divalent unsaturated hydrocarbon groups such as ethylenylene, propenylene, 2-propene-1-ylidene, 1-butenylene, 2-butenylene, 1,3-butadienylene, 1-pentenylene, 2-pentenylene, 1,3-pentadienylene, 1,4-pentadienylene, 1-hexenylene, 2-hexenylene, 3-hexenylene, 1,3-hexadienylene, 1,4-hexadienylene, 1,5-hexadienylene, 2,4-hexadienylene, 2,5-hexadienylene and 1,3,5-hexatrienylene. Particularly preferred among these compounds is a divalent unsaturated hydrocarbon having 3 or 4 carbon atoms such as 2-propene-1-ylidene group (in the case where a 6-membered ring is formed) and 1,3-butadienylene group (in the case where a 7-membered ring is formed), even more preferably 1,3-butadienylene group.

$R^7$, $R^9$, $R^{10}$ and $R^{12}$ each independently represent a hydrocarbon group having a carbon number of 1 to 4, a halogenated hydrocarbon group having a carbon number of 1 to 3 or a halogen atom. Specific examples of these groups include methyl, ethyl, n-propyl, i-propyl, t-butyl, fluoromethyl, chloromethyl, trifluoromethyl, fluoroethyl, chloroethyl, chlorine, and bromine. Preferred among these groups are methyl, ethyl, and chlorine.

$R^7$ and $R^9$ may be the same or different, and $R^{10}$ and $R^{12}$ may be the same or different. Preferably, the substituents on the same phenyl group ($R^7$ and $R^9$, $R^{10}$ and $R^{12}$) are the same. More preferably, all these substituents are halogen atoms.

$R^8$ and $R^{11}$ each independently represent a hydrocarbon group having a carbon number of 3 to 10, which may contain a silicon atom, with the proviso that phenyl groups and substituted phenyl groups are excluded to avoid duplication of Reference 5.

Specific examples of the aforementioned hydrocarbon group having a carbon number of 3 to 10 include propyl, butyl, pentyl, trialkylsilyl, and dialkylarylsilyl.

Branched hydrocarbon groups are particularly preferred. Specific examples of the branched hydrocarbon groups include i-propyl, i-butyl, s-butyl, t-butyl, 2-methylbutyl, 3-methylbutyl, 1,1-dimethylbutyl, 2,2-dimethylbutyl, 3,3-dimethylbutyl, 1,2-dimethyl butyl, 1,3-dimethylbutyl, 2,3-dimethylbutyl, 2-methylpentyl, 3-methylpentyl, 4-methylpentyl, 1,1-dimethylpentyl, 2,2-dimethylpentyl, 3,3-dimethylpentyl, 4,4-dimethylpentyl, 1,2-dimethylpentyl, 1,3-dimethylpentyl, 1,4-dimethylpentyl, 2,3-dimethylpentyl, 2,4-dimethylpentyl, and 3,4-dimethylpentyl.

Preferred among these branched hydrocarbon groups are branched alkyl groups having a carbon number of 3 to 6 such as i-propyl, t-butyl and 1,1-dimethylpropyl. Particularly preferred among these branched hydrocarbon groups are alkyl groups which are branched at its α-position such as t-butyl and 1,1-dimethylpropyl.

Specific examples of the aforementioned silicon-containing hydrocarbon group having a carbon number of 3 to 10 include trialkylsilyl groups such as trimethylsilyl, triethylsilyl, isopropyldimethylsilyl, t-butyldimethylsilyl, phenyldimethylsilyl, cyclotrimethylenemethylsilyl and cyclohexyldimethylsilyl; alkylsilylalkyl groups such as trimethylsilylmethyl and bis(trimethylsilyl)methyl; and dialkylarylsilyl groups such as dimethylphenylsilyl. Preferred among these silicon-containing hydrocarbon group having a carbon number of 3 to 10 are trialkylsilyl groups.

Particularly preferred among these trialkylsilyl groups are trimethylsilyl, triethylsilyl, and t-butyldimethylsilyl.

In formula (I), $R^{13}$ and $R^{14}$ each independently represent a hydrocarbon group having a carbon number of 1 to 8 or a halogenated hydrocarbon group having a carbon number of 1 to 8, each of which substitutes the hydrogen atom in the condensed hydrocarbon connecting group represented by $R^3$ or $R^6$.

Specific preferred examples of the hydrocarbon group having a carbon number of 1 to 8 include alkyl groups such as methyl, ethyl, n-propyl, i-propyl, n-butyl, i-butyl, s-butyl, t-butyl, n-pentyl, n-hexyl, cyclopropyl, cyclopentyl, cyclohexyl and methylcyclohexyl; alkenyl groups such as vinyl, propenyl, butenyl and cyclohexeny; arylalkyl groups such as benzyl and phenylethyl; arylakenyl groups such as transstyryl; and aryl groups such as phenyl, tollyl, dimethylphenyl and ethylphenyl.

Preferred examples of the halogen atom in the halogenated hydrocarbon group having a carbon number of 1 to 8 include fluorine, chlorine, bromine, and iodine. The aforementioned halogenated hydrocarbon group is a compound having a fluorine atom, if the halogen atom is a fluorine atom, substituted on arbitrary positions on the above-described hydrocarbon group.

Specific examples of the halogenated hydrocarbon group include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,4-difluorophenyl, 2,5-difluorophenyl, 2,6-difluorophenyl, 3,5-difluorophenyl, 2,4-dichlorophenyl, 2,5-dichlorophenyl, 2,6-dichlorophenyl, 3,5-dichlorophenyl, 2,4,6-trifluorophenyl, 2,4,6-trichlorophenyl, pentafluorophenyl, and pentachlorophenyl.

$R^{13}$ and $R^{14}$ each are preferably a alkyl group having a carbon number of 1 to 3.

In formula (I), j and k each represent an integer of 0 to 8. When j and k each are an integer of 2 or more, the plurality of $R^{13}$'s or $R^{14}$'s may be connected to each other to form a new annular structure. Preferably, j and k each are preferably an integer of 0 to 2, more preferably 0.

In formula (I), Q represents a bridging group connecting two cyclopentadienyl rings. As the group Q there may be used a bridging group in a known bridged metallocene-based transition metal compound.

Specific examples of Q include alkylene groups, arylalkylene groups, alkylsilylene groups, (alkyl) (aryl)silylene groups, and arylsilylene groups. These hydrocarbon groups may contain hetero atoms such as N, P, O, Si and halogen. These hydrocarbon groups each may be a bridging group obtained by replacing silicon by germanium. When two hydrocarbon groups are present on the aforementioned silylene group, they may be connected to each other to form an annular structure.

In some detail, a transition metal compound represented by formula (II) can be exemplified.

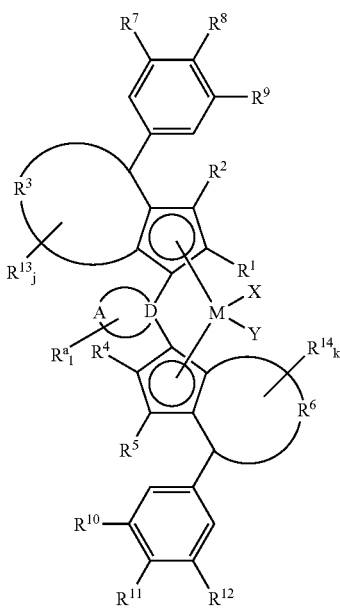

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3 or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, wherein $R^{13}$ substitutes a hydrogen atom in the hydrocarbon group represented by $R^3$, and $R^{14}$ substitutes a hydrogen atom in the hydrocarbon group represented by $R^6$;

j and k each represent an integer of from 0 to 8;

D represents a carbon atom, silicon atom, germanium atom or tin atom;

A represents a divalent saturated or unsaturated hydrocarbon group that has a carbon number of 3 to 5 and that forms a first ring with D;

$R^a$ represents a hydrocarbon group having a carbon number of 1 to 6 or a halogen-containing hydrocarbon group having a carbon number of 1 to 6, and $R^a$ is a substituent to be added to A, wherein a plurality of $R^a$'s, if any, may combine to form a second ring which is condensed to the first ring;

l represents an integer of 0 to 10;

X and Y each represent an auxiliary ligand which is σ-covalently bound, the auxiliary ligand being capable of reacting with a cocatalyst to develop an olefin-polymerizing capability; and M represents a transition metal belonging to the group IV in the periodic table.

A preferred example of A is a divalent saturated or unsaturated hydrocarbon group having four carbon atoms which forms a first ring with D. More preferably, A is an unsaturated hydrocarbon group having four carbon atoms.

A preferred example of $R^a$ is an alkyl or phenyl group. A preferred example of l is an integer of from 2 to 4.

When there is a plurality of $R^a$'s, it is preferred that they combine to form an unsaturated ring which is condensed to the first ring, and the unsaturated ring may further have substituents. It is particularly preferred that $R_a$'s combine to form a benzene ring which may have substituents.

When $R^a$'s combine to a ring, $R_a$'s may be not only adjacent to each other but also be apart from each other so far as they can form a ring.

Particularly preferred among these bridging groups are dimethylsilylene, dimethylgermylene, and silafluorenyl.

X and Y each represent an auxiliary ligand which is σ-covalently bound, the auxiliary ligand being capable of reacting with a cocatalyst to develop an olefin-polymerizing capability. Each of X and Y independently represents a hydrogen atom, halogen atom, a hydrocarbon group having a carbon number 1 to 20, a halogenated hydrocarbon group having a carbon number of 1 to 20, a silicon-containing hydrocarbon group having a carbon number of 1 to 20, an oxygen-containing hydrocarbon group having a carbon number of 1 to 20, an amino group or a nitrogen-containing hydrocarbon group having a carbon number of 1 to 20.

Examples of the halogen atom include fluorine atom, chlorine atom, bromine atom, and iodine atom.

X and Y each are preferably a hydrogen atom, a halogen atom, a hydrocarbon group having a carbon number of 1 to 20 or a nitrogen-containing hydrocarbon group having a carbon number of 1 to 20, more preferably a halogen atom, a hydrocarbon group having a carbon number of 1 to 20 or a nitrogen-containing hydrocarbon group having a carbon number of 1 to 20, particularly chlorine atom, methyl group, i-butyl group, phenyl group, benzyl group, dimethylamino group or diethylamino group.

M represents a transition metal belonging to the group IV in the periodic table, preferably titanium, zirconium or hafnium, particularly zirconium or hafnium.

1.-(4) Synthesis of Transition Metal Compound

The transition metal compound of the present invention can be synthesized by a method which is arbitrary concerning the substituents and the mode of bonding. A representative synthesis scheme of the transition metal compound is shown in the following reaction formula.

For example, in the case where $R^3$ and $R^6$ each are 1,3-butadienylene group (that is, in the case where the structure formed by $R^3$, $R^6$, carbon atoms at the 4-position and 4'-position and cyclopentadienyl is an azulenyl ring), the transition metal compound can be synthesized as follows.

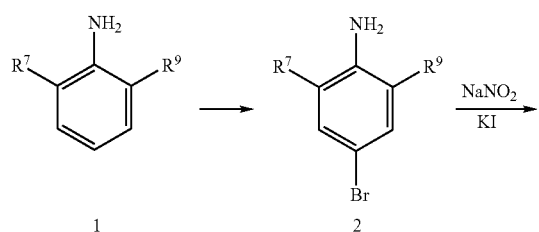

-continued

An aniline 1 having $R^7$ and $R^9$ is subjected to bromination with 2,4,4,6-tetrabromo-2,5-cyclohexadienone or the like in a manner described in "Organic Synthesis", 1976, vol. 55, page 20 to obtain an intermediate product 2. The intermediate product 2 is then subjected to diazo reaction with sodium nitrite and reaction with potassium iodide in a manner described in "Bull. Chem. Soc. Jpn.", 2001, vol. 74, page 2,207 to obtain an intermediate product 3. The intermediate product 3 is then reacted with alkyl lithium so that the iodine atoms are selectively lithiated and reacted with $R^8$—Cl such as trimethylsilyl chloride to obtain an intermediate product 4. The intermediate product 4 is then subjected to lithiation with an alkyl lithium in a manner as described in JP-A-11-240909 to obtain an intermediate product 5. The intermediate product 5 is then reacted with a substituted azulene so that it is added to the substituted azulene, and subsequently reacted with $QCl_2$ such as dimethyldichlorosilane to obtain an intermediate product 6. The intermediate product 6 is then subjected to lithiation with an alkyl lithium in a manner as described in JP-A-11-240909 and reacted with $MCl_4$ to obtain the desired product 7.

Alternatively, in the case where $R^3$ and $R^6$ each are 2-propene-1-ylidene (that is, in the case where the structure formed by $R^3$, $R^6$, carbon atoms at the 4-position and 4'-position and cyclopentadienyl is an indenyl ring), the transition metal compound can be synthesized as follows.

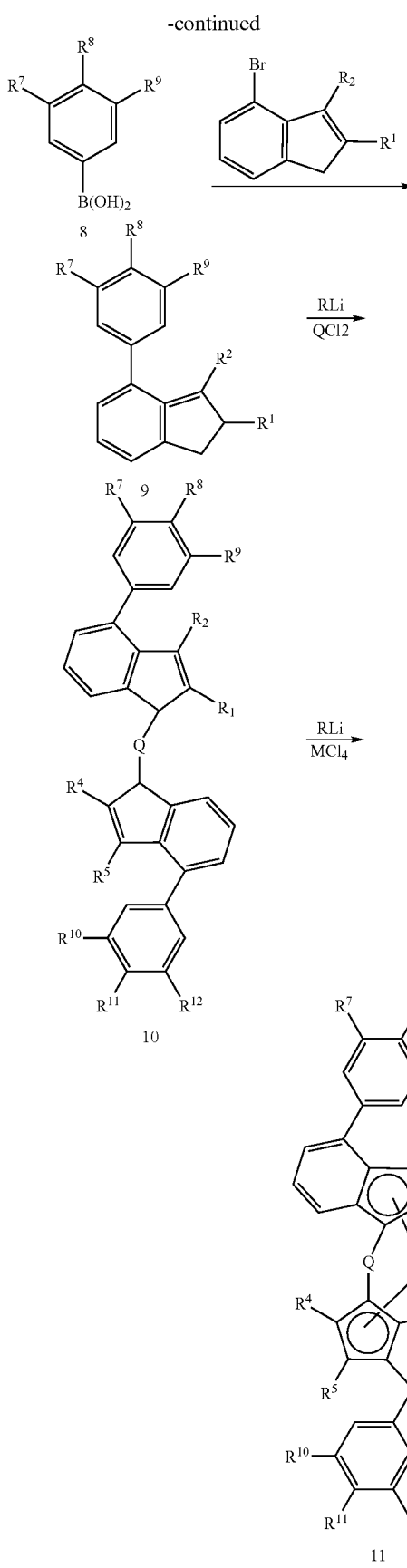

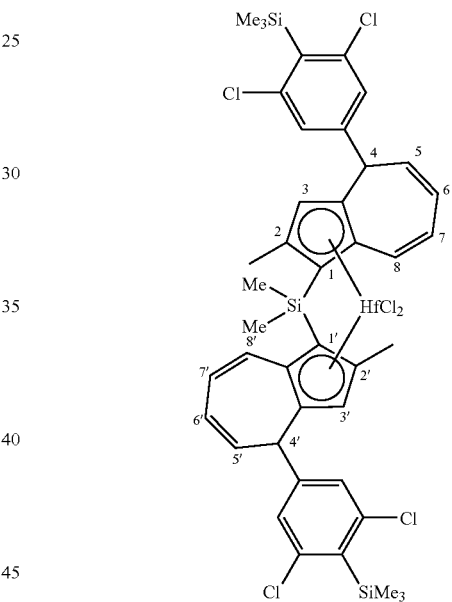

A compound 4 which is a starting material is subjected to lithiation with an alkyl lithium and then reacted with a trialkoxyborane to obtain an intermediate product 8. The intermediate product 8 is then subjected to coupling reaction with 4-bromo substituted indene in the presence of a palladium catalyst or the like to obtain an intermediate product 9. The reaction for obtaining the desired product 11 from the intermediate product 9 can be conducted in the same manner as in the synthesis of the product 7.

1.-(5) Specific Examples of Transition Metal Compound

Specific preferred examples of the transition metal compound of the present invention are given below. Concerning stereostructure, these specific preferred examples include both the asymmetric compound and symmetric compound as above-defined.

Hafnium dichloride is selected as a representative of transition metal compound. The nomenclature of hafnium dichloride having the following structural formula will be exemplified as follows.

The compound having the aforementioned structural formula is referred to as "dichloro(1,1'-dimethyl silylenebis{2-methyl-4-(4-trimethylsilyl-3,5-dichloriphenyl 1)-4H-azulenyl})hafnium".

Since the main constitution of the present invention is a novel transition metal compound, it is essential that a large number of transition metal compounds is exemplified. However, in order to simplify the description of the specification, the exemplification of transition metal compounds is limited to main representative examples to avoid complicated description. Accordingly, all transition metal compounds other than those listed below are included in the scope described in the claims of the present invention.

For example, in the following specific examples, it is considered that compounds obtained by replacing hafnium by titanium or zirconium and dichloride by other X and Y and substituents on the annular structure by other substituents are exemplified.

The following examples are listed in paragraphs by similarity.

(1) Dichloro(1,1'-dimethylsilylenebis{2-methyl-4-(4-trimethylsilyl-3,5-dichlorophenyl)-4H-azulenyl))hafnium
(2) Dichloro(1,1'-dimethylsilylenebis{2-methyl-4-(4-trimethylsilyl-3,5-difluorophenyl)-4H-azulenyl})hafnium
(3) Dichloro(1,1'-dimethylsilylenebis{2-methyl-4-(4-trimethylsilyl-3,5-dimethylphenyl)-4H-azulenyl})hafnium
(4) Dichloro(1,1'-dimethylsilylenebis{2-methyl-4-(4-trimethylsilyl-3,5-diethylphenyl)-4H-azulenyl})hafnium
(5) Dichloro(1,1'-dimethylsilylenebis{2-methyl-4-(4-trimethylsilyl-3,5-di-1-propylphenyl)-4H-azulenyl})hafnium
(6) Dichloro(1,1'-dimethylsilylenebis{2-methyl-4-(4-trimethylsilyl-3-chloro-5-methylphenyl)-4H-azulenyl}) hafnium
(7) Dichloro(1,1'-dimethylsilylenebis{2-methyl-4-(4-trimethylsilyl-3-chloro-5-fluorophenyl)-4H-azulenyl}) hafnium
(8) Dichloro(1,1'-dimethylsilylenebis{2-methyl-4-(4-trimethylsilyl-3-chloro-5-ethylphenyl)-4H-azulenyl}) hafnium
(9) Dichloro(1,1'-dimethylsilylenebis{2-methyl-4-(4-trimethylsilyl-3-methyl-5-ethylphenyl)-4H-azulenyl}) hafnium
(10) Dichloro(1,1'-dimethylsilylenebis{2-methyl-4-(4-triethylsilyl-3,5-dichlorophenyl)-4H-azulenyl})hafnium
(11) Dichloro(1,1'-dimethylsilylenebis{2-methyl-4-(4-dimethylphenylsilyl-3,5-dichlorophenyl}-4H-azulenyl)) hafnium
(12) Dichloro(1,1'-dimethylsilylenebis{2-methyl-4-(4-i-propyl-3,5-dichlorophenyl)-4H-azulenyl})hafnium
(13) Dichloro(1,1'-dimethylsilylenebis{2-methyl-4-(4-t-butyl-3,5-dichlorophenyl)-4H-azulenyl})hafnium
(14) Dichloro(1,1'-dimethylsilylenebis{2-methyl-4-(4-t-butyl-3,5-difluorophenyl)-4H-azulenyl})hafnium
(15) Dichloro(1,1'-dimethylsilylenebis{2-methyl-4-(4-t-butyl-3,5-dimethylphenyl)-4H-azulenyl})hafnium
(16) Dichloro(1,1'-dimethylsilylenebis{2-methyl-4-(4-t-butyl-3,5-diethylphenyl)-4H-azulenyl})hafnium
(17) Dichloro(1,1'-dimethylsilylenebis{2-methyl-4-(4-t-butyl-3-chloro-5-methylphenyl)-4H-azulenyl})hafnium
(18) Dichloro(1,1'-dimethylsilylenebis{2-methyl-4-(4-t-butyl-3-chloro-5-fluorophenyl)-4H-azulenyl})hafnium
(19) Dichloro(1,1'-dimethylsilylenebis{2-methyl-4-(4-t-butyl-3-chloro-5-ethylphenyl)-4H-azulenyl})hafnium
(20) Dichloro(1,1'-dimethylsilylenebis{2-methyl-4-(4-t-butyl-3-methyl-5-ethylphenyl)-4H-azulenyl})hafnium
(21) Dichloro(1,1'-dimethylsilylenebis{2-ethyl-4-(4-trimethylsilyl-3,5-dichlorophenyl)-4H-azulenyl})hafnium
(22) Dichloro(1,1'-dimethylsilylenebis{2-ethyl-4-(4-trimethylsilyl-3,5-difluorophenyl)-4H-azulenyl})hafnium
(23) Dichloro(1,1'-dimethylsilylenebis{2-ethyl-4-(4-trimethylsilyl-3,5-dimethylphenyl)-4H-azulenyl})hafnium
(24) Dichloro(1,1'-dimethylsilylenebis{2-ethyl-4-(4-trimethylsilyl-3,5-diethylphenyl)-4H-azulenyl})hafnium
(25) Dichloro(1,1'-dimethylsilylenebis{2-ethyl-4-(4-trimethylsilyl-3,5-di-i-propylphenyl)-4H-azulenyl})hafnium
(26) Dichloro(1,1'-dimethylsilylenebis{2-ethyl-4-(4-trimethylsilyl-3-chloro-5-methylphenyl)-4H-azulenyl}) hafnium
(27) Dichloro(1,1'-dimethylsilylenebis{2-ethyl-4-(4-trimethylsilyl-3-chloro-5-fluorophenyl)-4H-azulenyl}) hafnium
(28) Dichloro(1,1'-dimethylsilylenebis{2-ethyl-4-(4-trimethylsilyl-3-chloro-5-ethylphenyl)-4H-azulenyl}) hafnium
(29) Dichloro(1,1'-dimethylsilylenebis{2-ethyl-4-(4-trimethylsilyl-3-methyl-5-ethylphenyl)-4H-azulenyl}) hafnium
(30) Dichloro(1,1'-dimethylsilylenebis{2-ethyl-4-(4-t-butyl-3,5-dichlorophenyl)-4H-azulenyl})hafnium
(31) Dichloro(1,1'-dimethylsilylenebis{2-ethyl-4-(4-t-butyl-3,5-difluorophenyl)-4H-azulenyl})hafnium
(32) Dichloro(1,1'-dimethylsilylenebis{2-ethyl-4-(4-t-butyl-3,5-dimethylphenyl)-4H-azulenyl})hafnium
(33) Dichloro(1,1'-dimethylsilylenebis{2-ethyl-4-(4-t-butyl-3,5-diethylphenyl)-4H-azulenyl})hafnium
(34) Dichloro(1,1'-dimethylsilylenebis{2-ethyl-4-(4-t-butyl-3-chloro-5-methylphenyl)-4H-azulenyl})hafnium
(35) Dichloro(1,1'-dimethylsilylenebis{2-ethyl-4-(4-t-butyl-3-chloro-5-fluorophenyl)-4H-azulenyl})hafnium
(36) Dichloro(1,1'-dimethylsilylenebis{2-ethyl-4-(4-t-butyl-3-chloro-5-ethylphenyl)-4H-azulenyl})hafnium
(37) Dichloro(1,1'-dimethylsilylenebis{2-ethyl-4-(4-t-butyl-3-methyl-5-ethylphenyl)-4H-azulenyl})hafnium
(38) Dichloro(1,1'-dimethylsilylenebis{2-ethyl-4-(4-triethylsilyl-3,5-dichlorophenyl)-4H-azulenyl})hafnium
(39) Dichloro(1,1'-dimethylsilylenebis{2-ethyl-4-(4-dimethylsilyl-3,5-dichlorophenyl)-4H-azulenyl})hafnium
(40) Dichloro(1,1'-dimethylsilylenebis{2-ethyl-4-(4-1-propyl-3,5-dichlorophenyl)-4H-azulenyl})hafnium
(41) Dichloro(1,1'-dimethylsilylenebis{2-i-propyl-4-(4-trimethylsilyl-3,5-dichlorophenyl)-4H-azulenyl})hafnium
(42) Dichloro(1,1'-dimethylsilylenebis{2-i-propyl-4-(4-trimethylsilyl-3,5-difluorophenyl)-4H-azulenyl})hafnium
(43) Dichloro(1,1'-dimethylsilylenebis{2-i-propyl-4-(4-trimethylsilyl-3,5-dimethylphenyl)-4H-azulenyl})hafnium
(44) Dichloro(1,1'-dimethylsilylenebis{2-i-propyl-4-(4-trimethylsilyl-3-chloro-5-methylphenyl)-4H-azulenyl}) hafnium
(45) Dichloro(1,1'-dimethylsilylenebis{2-i-propyl-4-(4-t-butyl-3,5-dichlorophenyl)-4H-azulenyl})hafnium
(46) Dichloro(1,1'-dimethylsilylenebis{2-i-propyl-4-(4-t-butyl-3,5-difluorophenyl)-4H-azulenyl})hafnium
(47) Dichloro(1,1'-dimethylsilylenebis{2-i-propyl-4-(4-t-butyl-3,5-dimethylphenyl)-4H-azulenyl})hafnium
(48) Dichloro(1,1'-ethylenebis{2-methyl-4-(4-trimethylsilyl-3,5-dichlorophenyl)-4H-azulenyl})hafnium
(49) Dichloro(1,1'-ethylenebis{2-methyl-4-(4-trimethylsilyl-3,5-dimethylphenyl)-4H-azulenyl})hafnium
(50) Dichloro(1,1'-ethylenebis{2-methyl-4-(4-trimethylsilyl-3-chloro-5-methylphenyl)-4H-azulenyl})hafnium
(51) Dichloro(1,1'-dimethylgermylenebis{2-methyl-4-(4-trimethylsilyl-3,5-dichlorophenyl)-4H-azulenyl}) hafnium
(52) Dichloro(1,1'-dimethylgermylenebis{2-methyl-4-(4-trimethylsilyl-3,5-dimethylphenyl)-4H-azulenyl}) hafnium
(53) Dichloro(1,1'-dimethylgermylenebis{2-methyl-4-(4-trimethylsilyl-3-chloro-5-methylphenyl)-4H-azulenyl}) hafnium
(54) Dichloro(1,1'-silafluorenylbis{2-methyl-4-(4-trimethylsilyl-3,5-dichlorophenyl)-4H-azulenyl})hafnium
(55) Dichloro(1,1'-silafluorenylbis{2-methyl-4-(4-trimethylsilyl-3,5-dimethylphenyl)-4H-azulenyl})hafnium
(56) Dichloro(1,1'-silafluorenylbis{2-methyl-4-(4-trimethylsilyl-3-chloro-5-methylphenyl)-4H-azulenyl})hafnium

(57) Dichloro(1,1'-dimethylsilylene{2-methyl-4-(4-trimethylsilyl-3,5-dichlorophenyl)-4H-azulenyl}{2-methyl-4-(4-trimethylsilyl-3,5-dimethylphenyl)-4H-azulenyl})hafnium

(58) Dichloro(1,1'-dimethylsilylene{2-ethyl-4-(4-trimethylsilyl-3,5-dichlorophenyl)-4H-azulenyl}{2-ethyl-4-(4-trimethylsilyl-3,5-dimethylphenyl)-4H-azulenyl})hafnium

(59) Dichloro(1,1'-dimethylsilylene{2-methyl-4-(4-trimethylsilyl-3,5-dichlorophenyl)-4H-azulenyl}{2-ethyl-4-(4-trimethylsilyl-3,5-dimethylphenyl)-4H-azulenyl})hafnium

(60) Dichloro(1,1'-dimethylsilylenebis{2-methyl-4-(4-trimethylsilyl-3,5-dichlorophenyl)-indenyl})hafnium

(61) Dichloro(1,1'-dimethylsilylenebis{2-methyl-4-(4-trimethylsilyl-3,5-dimethylphenyl)-indenyl})hafnium

(62) Dichloro(1,1'-dimethylsilylenebis{2-ethyl-4-(4-trimethylsilyl-3,5-dichlorophenyl)-indenyl})hafnium

(63) Dichloro(1,1'-dimethylsilylenebis{2-ethyl-4-(4-trimethylsilyl-3,5-dimethylphenyl)-indenyl})hafnium

(64) Dichloro(1,1'-dimethylsilylene{2-methyl-4-(4-trimethylsilyl-3,5-dichlorophenyl)-4H-azulenyl}{2-methyl-4-(4-trimethylsilyl-3,5-dichlorophenyl)-4H-indenyl})hafnium

(65) Dichloro(1,1'-dimethylsilylene{2-methyl-4-(4-trimethylsilyl-3,5-dichlorophenyl)-4H-azulenyl}{2-methyl-4-(4-trimethylsilyl-3,5-dimethylphenyl)-4H-indenyl})hafnium

(66) Dichloro(1,1'-dimethylsilylene{2-ethyl-4-(4-trimethylsilyl-3,5-dichlorophenyl)-4H-azulenyl}{2-ethyl-4-(4-trimethylsilyl-3,5-dichlorophenyl)-indenyl})hafnium

(67) Dichloro(1,1'-dimethylsilylene{2-methyl-4-(4-trimethylsilyl-3,5-dichlorophenyl)-4H-azulenyl}{2-ethyl-4-(4-trimethylsilyl-3,5-dichlorophenyl)-indenyl})hafnium.

As previously mentioned, in the aforementioned series of compounds, compounds obtained by replacing one or both of the two chlorine atoms corresponding to X and Y in formula (I) by hydrogen atom, fluorine atom, bromine atom, iodine atom, methyl group, phenyl group, fluorophenyl group, benzyl group, methoxy group, dimethylamino group, diethylamino group or the like may be exemplified. Further, as exemplified above, these compounds may have different ligands such as indenyl ring and azulenyl ring in the same molecule.

Specific examples of the compound represented by formula (II) include those obtained by replacing the bridging group of the compounds represented by formulae (1) to (67) by bridging groups represented by the following formulae (68) to (91). Further, compounds obtained by replacing Si in the following formulae by C, Ge or Sn may be exemplified.

(Me=methyl; iPr=isopropyl; Ph=phenyl)

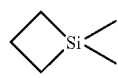
(68)

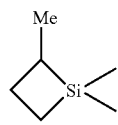
(69)

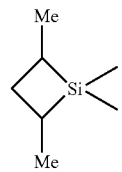
(70)

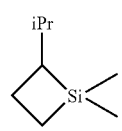
(71)

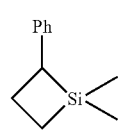
(72)

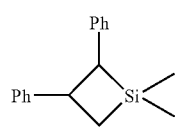
(73)

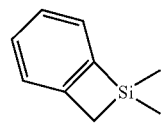
(74)

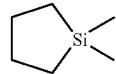
(75)

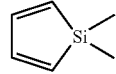
(76)

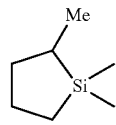
(77)

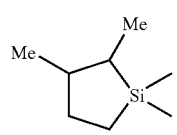
(78)

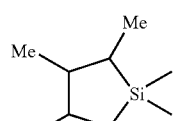
(79)

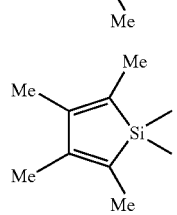
(80)

-continued

(81) 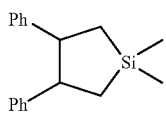

(82) 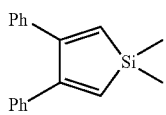

(83) 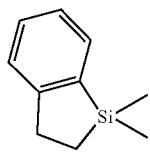

(84) 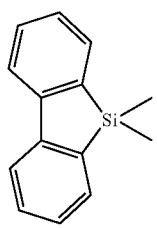

(85) 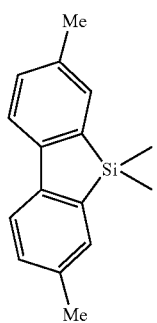

(86) 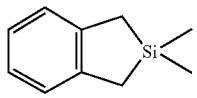

(87) 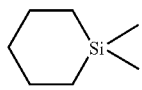

(88) 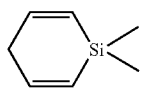

(89) 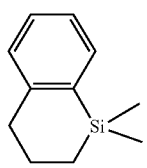

-continued

(90) 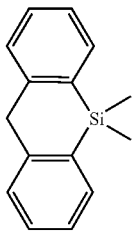

(91) 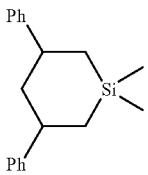

As previously mentioned, in the aforementioned series of compounds, compounds obtained by replacing one or both of the two chlorine atoms corresponding to X and Y in formula (II) by hydrogen atom, fluorine atom, bromine atom, iodine atom, methyl group, phenyl group, fluorophenyl group, benzyl group, methoxy group, dimethylamino group, diethylamino group or the like may be exemplified. Further, as exemplified above, rings having different numbers of members may be bridged, for example, an indenyl ring and an azulenyl ring may be bridged.

2. Olefin Polymerization Catalyst

The catalyst component for olefin polymerization made of the transition metal compound of the present invention can be used to form an olefin polymerization catalyst. The catalyst component for olefin polymerization of the present invention is preferably used as a polymerization catalyst such as the following olefin polymerization catalyst (1) and olefin polymerization catalyst (2) comprising the catalyst component for olefin polymerization as component (A).

2.-(1) Olefin Polymerization Catalyst (1)

The olefin polymerization catalyst (1) is a catalyst comprising components (A) and (B). The olefin polymerization catalyst (1) may include a carrier (C) or an organic aluminum compound.

Specific examples of the component (B) include the following compounds (B-1) to (B-3):

(B-1): Aluminum oxy compound;

(B-2): Ionic compound capable of reacting with the component (A) to convert the component (A) to a cation, or Lewis acid; and (B-3): Solid acid.

Referring to the aluminum oxy compound (B-1), it is well known that an aluminum oxy compound can activate a metallocene complex. Specific examples of such a compound include compounds represented by the following general formulae.

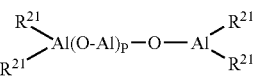 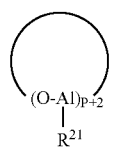

-continued

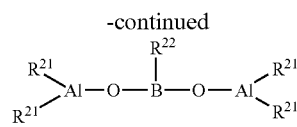

wherein $R^{21}$ represents a hydrogen atom or hydrocarbon group, preferably a hydrocarbon group having a carbon number of 1 to 10, particularly 1 to 6; a plurality of $R^{21}$'s may be the same or different; and p represents an integer of 0 to 40, preferably 2 to 30.

Among the aforementioned compounds, those represented by the first and second formulae are also referred to as "aluminoxane". Preferred among these compounds are methyl aluminoxane and methylisobutyl aluminoxane. These aluminoxanes may be used in combination of the same or different groups of compounds. These aluminoxanes can be prepared under various known conditions.

The compound represented by the third formula can be obtained by reacting one or more trialkyl aluminums with an alkylboronic acid represented by the general formula $R^{22}B(OH)_2$ at a molar ratio of 10:1 to 1:1. In the general formula $R^{22}B(OH)_2$, $R^{22}$ represents a hydrocarbon group having a carbon number of 1 to 10, preferably 1 to 6.

The compound (B-2) is an ionic compound capable of reacting with the component (A) to convert the component (A) to a cation, or Lewis acid. Examples of such an ionic compound include complexes of cations such as carbonium cation and ammonium cation with organic boron compounds such as triphenyl boron, tris(3,5-difluorophenyl) boron and tris(pentafluorophenyl) boron.

Examples of the aforementioned Lewis acid include various organic boron compounds such as tris (pentafluorophenyl) boron. Other examples of the aforementioned Lewis acid include metal halide compounds such as aluminum chloride and magnesium chloride.

Some of the aforementioned Lewis acids may be considered ionic compounds capable of reacting with the component (A) to convert the component (A) to a cation. Metallocene complexes comprising the aforementioned non-coordination boron compounds are exemplified in JP-A-3-234709, JP-A-5-247128, etc.

Examples of the solid acid (B-3) include alumina, silica-alumina, and silica-magnesia.

In the olefin polymerization catalyst (1) of the present invention, the carrier (C) as an arbitrary component is a particulate carrier made of an inorganic or organic compound having a particle diameter of normally from 5 µm to 5 mm, preferably from 10 µm to 2 mm.

Examples of the aforementioned inorganic carrier include oxides such as $SiO_2$, $Al_2O_3$, MgO, ZrO, $TiO_2$, $B_2O_3$ and ZnO, and composite oxides such as $SiO_2$—MgO, $SiO_2$—$Al_2O_3$, $SiO_2$—$TiO_2$, $SiO_2$—$Cr_2O_3$ and $SiO_2$—$Al_2O_3$—MgO.

Examples of the aforementioned organic carrier include porous particulate polymer carriers made of an α-olefin (co)polymer having a carbon number of 2 to 14, such as ethylene, propylene, 1-butene and 4-methyl-1-pentene; an aromatic unsaturated hydrocarbon (co)polymer such as styrene and divinylbenzene, etc. Such a particulate material has a specific surface area of normally from 20 to 1,000 m²/g, preferably from 50 to 700 m²/g, and a pore volume of normally 0.1 cm³/g or more, preferably 0.3 cm³/g or more, more preferably 0.8 cm³/g or more.

The olefin polymerization catalyst (1) of the invention may comprise, as arbitrary components other than the particulate carrier, active hydrogen-containing compounds such as $H_2O$, methanol, ethanol and butanol; electron donative compounds such as ether, ester and amine; and alkoxy-containing compounds such as phenyl borate, dimethylmethoxy aluminum, phenyl phosphate, tetraethoxysilane and diphenyldimethoxysilane.

Other examples of arbitrary components include tri-lower alkyl aluminum such as trimethyl aluminum, triethyl aluminum and triisobutyl aluminum; halogen-containing alkyl aluminum such as diethyl aluminum chloride, diisobutyl aluminum chloride and methyl aluminum sesquichloride; alkyl aluminum hydrides such as diethyl aluminum hydride; alkoxy-containing alkyl aluminum such as diethyl aluminum ethoxide and dimethyl aluminum butoxide; and aryloxy-containing alkyl aluminum such as diethyl aluminum phenoxide.

In the olefin polymerization catalyst (1) of the present invention, the aluminum oxy compound, the ionic compound capable of reacting with the component (A) to convert the component (A) to a cation and the Lewis acid are used as component (B) singly or in proper combination. Though being arbitrary components, one or more of the aforementioned lower alkyl aluminum, halogen-containing alkyl aluminum, alkyl aluminum hydrides, alkoxy-containing alkyl aluminum and aryloxy-containing alkyl aluminum are preferably incorporated in the olefin polymerization catalyst (1) in combination with aluminum oxy compounds, ionic compounds or Lewis acids.

The olefin polymerization catalyst (1) of the present invention can be prepared by allowing the aforementioned components (A) and (B) to come in contact with each other in the presence or absence of a monomer to be polymerized inside or outside the polymerization tank. In some detail, the components (A) and (B) and optionally the component (C) and other components may be separately introduced into the polymerization tank. Alternatively, the components (A) and (B) may be previously allowed to come in contact with each other before being introduced into the polymerization tank. Alternatively, a mixture of the components (A) and (B) may be incorporated in the component (C) before being introduced into the polymerization tank.

The contact of the aforementioned various components may be effected in an inert hydrocarbon solvent such as pentane, hexane, heptane, toluene and xylene in an inert gas such as nitrogen. The contact temperature is preferably from −20° C. to the boiling point of the solvent, particularly from room temperature to the boiling point of the solvent. The catalyst thus prepared may or may not be cleaned before use. Further, the catalyst thus prepared may be combined with other components as necessary before use.

2.-(2) Olefin Polymerization Catalyst (2)

The olefin polymerization catalyst (2) is described hereinafter. The olefin polymerization catalyst (2) is a catalyst comprising the component (A), the component (D) and optionally the component (E).

The component (D) is selected from the group consisting of ion-exchanging layered compounds and inorganic silicates. The component (E) is an organic aluminum compound.

Among the components (D), the ion-exchanging layered compound accounts for the majority of clay minerals and is preferably-an ion-exchanging layered silicate.

The ion-exchanging layered silicate (hereinafter simply referred to as "silicate") to be used herein is a silicate compound having a crystalline structure which comprises planes formed by ionic bond or the like, the planes being superposed on each other by bonding, and the silicate compound containing exchangeable ions. Most silicates occur naturally as a main component of clay mineral and thus often contain foreign matters other than ion-exchanging layered silicates (e.g., quartz, cristobalite). However, these foreign matters may be included in the silicate. As the silicate there may be used any known silicate. Specific examples of the silicate employable herein include the following layered silicates described in Haruo Shiromizu, "Nendo Kobutsugaku (Studies of Clay Mineral)", Asakura Shoten, 1995.

2:1 Type Minerals:

Smectites such as montmorillonite, sauchonite, beidelite, nontronite, saponite, hectorite and stevensite; vermiculites such as vermiculit; micas such as mica, illite, sericite and clauconite; pyrophyllite-talc such as pyrophyllite and talc; chlorites such as Mg chlorite, etc.

2:1 Type Ribbon Type Minerals:

Sepiolite, palygorskite, etc.

The silicate to be used as a starting material in the present invention may be a layered silicate having the aforementioned mixed layers. In the present invention, the silicate preferably comprises as a main component a silicate having a 2:1 type structure. Smectites are more proffered, and montmorillonite is particularly preferred. The silicate to be used in the present invention, if it has been obtained as a natural product or industrial material, may not be treated before use but is preferably subjected to chemical treatment before use. Specific examples of chemical treatment include acid treatment, alkali treatment, salt treatment, and treatment with organic material. These treatments may be effected in combination. In the present invention, the treatment conditions are not specifically limited and any known treatment conditions may be used.

Further, these ion-exchanging layered silicates normally contain adsorbed water and interlayer water and thus are preferably heated and dehydrated in the stream of inert gas to remove water content therefrom before use.

In the olefin polymerization catalyst (2) of the present invention, an example of the organic aluminum compound as arbitrary component (E) is represented by the following formula:

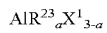

$$AlR^{23}{}_aX^1{}_{3-a}$$

wherein $R^{23}$ represents a hydrocarbon group having a carbon number of 1 to 20; $X^1$ represents a hydrogen atom, halogen atom, alkoxy group or siloxy group; and the suffix a represents a number of from more than 0 to not more than 3. Specific examples of the organic aluminum compound represented by the aforementioned formula include trialkyl aluminum such as trimethyl aluminum, triethyl aluminum, tripropyl aluminum and triisobutyl aluminum; and halogen- or alkoxy-containing alkyl aluminum such as diethyl aluminum monochloride and diethyl aluminum monomethoxide. Preferred among these organic aluminum compounds is trialkyl aluminum.

As the component (E) to be incorporated in the olefin polymerization catalyst (2) of the present invention there may be used an aluminoxane such as methyl aluminoxane besides the organic aluminum compound represented by the aforementioned formula. Further, the aforementioned organic aluminum compound and aluminoxane may be used in combination.

The olefin polymerization catalyst (2) of the present invention can be prepared by the same method as described with reference to the olefin polymerization catalyst (1). In this case, the process for bringing the components (A) and (D) into contact with the arbitrary component (E) is not specifically limited, but the following processes can be exemplified.

(1) Process which comprises bringing the components (A) and (D) into contact with each other;

(2) Process which comprises bringing the components (A) and (D) into contact with each other, and then adding the arbitrary component (E) to the mixture;

(3) Process which bringing the component (A) and the arbitrary component (E) into contact with each other, and then adding the component (D) to the mixture;

(4) Process which bringing the component (D) and the arbitrary component (E) into contact with each other, and then adding the component (A) to the mixture; and (5) Process which comprises bringing the components (A), (D) and (E) into contact with each other at the same time.

The contact of these components may be effected not only during the preparation of catalyst but also during the prepolymerization by olefin or olefin polymerization. During or after the contact of the aforementioned components, a polymer such as polyethylene and polypropylene and a solid inorganic oxide such as silica and alumina may be present or brought into contact with these components.

Further, the contact of the aforementioned components may be effected in an inert hydrocarbon solvent such as pentane, hexane, heptane, toluene and xylene in an inert gas such as nitrogen. The contact is preferably effected at a temperature of from –20° C. to the boiling point of the solvent, particularly from room temperature to the boiling point of the solvent.

2.-(3) Amount of Catalyst Component to be Used, Others

The component (A) and the component (B) or (D) may be used at an optimum ratio depending on their combination.

When the component (B) is an aluminum oxy compound, the molar ratio of Al/transition metal is normally from not smaller than 10 to not greater than 100,000, preferably from not smaller than 100 to not greater than 20,000, particularly from not smaller than 100 to not greater than 10,000. On the other hand, when as the component (B) there is used an ionic compound or Lewis acid, the molar ratio to transition metal is normally from 0.1 to 1,000, preferably from 0.5 to 100, more preferably from 1 to 50.

When as the component (B) there is used a solid acid or as the component (D) there is used an ion-exchanging layered compound, the transition metal complex is used in an amount of from 0.001 to 10 mmol, preferably from 0.001 to 1 mmol per g of the component (B) or (D).

The above defined ratio of components is merely an ordinary example. It is natural that the present invention should not be limited to the above defined value so far as the catalyst can meet the requirements.

The catalyst for production of polyolefin comprising a transition metal complex and a cocatalyst may be supported on a carrier as necessary before used as a catalyst for olefin polymerization (main polymerization). The supported catalyst is then used for prepolymerization of an olefin such as ethylene, propylene, 1-butene, 1-hexene, 1-octene, 4-methyl-1-pentene, 3-methyl-1-butene, vinyl cyloalkane and styrene in a small amount. The prepolymerization can be carried out by any known method.

3. Olefin Polymerization

3.-(1) Olefin to be Polymerized

The olefin which can be polymerized in the presence of the olefin polymerization catalyst of the present invention is essentially an α-olefin. Examples of such an α-olefin include propylene, butene-1,3-methybutene-1, 3-methylpentene-1, 4-methylpentene-1, conjugated dienes such as vinyl cyloalkane and butadiene, non-conjugated dienes such as 1,5-hexadiene, styrene, and derivatives thereof. Particularly preferred among these α-olefins is propylene.

The invention can be applied to random copolymerization or block copolymerization besides homopolymerization. Examples of comonomers to be copolymerized include ethylene besides the aforementioned olefins.

3.-(2) Polymerization Reaction

The polymerization reaction is preferably carried out by a gas phase polymerization process in the presence of an inert hydrocarbon such as butane, pentane, hexane, heptane, toluene and cyclohexane or a solvent such as liquefied α-olefin, or in substantial absence of liquid phase such as solvent and monomer. The gas phase polymerization may be effected using a reactor such as agitated fluidized bed reactor having a fluidized bed, an agitated bed and an agitator.

The conditions such as polymerization temperature and polymerization pressure are not specifically limited, but the polymerization temperature is normally from −50° C. to 350° C., preferably from 0° C. to 300° C., and the polymerization pressure is normally from atmospheric pressure to about 2,000 kgf/cm$^2$, preferably from atmospheric pressure to 1,500 kgf/cm$^2$, more preferably from atmospheric pressure to 1,300 kgf/cm$^2$. Hydrogen may be present in the polymerization system as a molecular weight adjustor.

The present invention is further described in the following examples, but the invention is not limited thereto.

In the following examples, both the catalyst synthesis step and the polymerization step were conduced in an atmosphere of purified nitrogen. The solvent to be used was dehydrated by MS (molecular sieve)-4A, and then bubbled with purified nitrogen to undergo deaeration. The activity per solid catalyst component was represented by catalytic activity (unit: g-polymer/g-cat·hr) and the activity per complex component was represented by complex activity (unit: g-polymer/g-complex·hr).

(1) Measurement of MFR (Melt Flow Rate):

To 6 g of a polymer was added 6 g of an acetone solution (0.6% by weight) of a heat stabilizer (BHT). Subsequently, the polymer was dried, and then packed in a melt indexer (230° C.) which was then allowed to stand at a load of 2.16 kg for 5 minutes. Thereafter, the extrusion rate of the polymer was measured. The measured value was then converted to amount per 10 minutes as MFR (unit: g/10 min, JIS K7210).

(2) Measurement of Melting Point:

Using a Type TA2000 DSC (produced by Du Pont Inc.) or Type DSC6200 device (produced by Seiko Instrument Co., Ltd.), the specimen was once heated and cooled at a rate of 10° C./min between 20° C. and 200° C., and then measured for melting point when heated second time at a rate of 10° C./min.

EXAMPLE-1

(1) Metallocene Complex (a) Synthesis of dichloro(1,1'-dimethylsilylenebis{2-ethyl-4-(4-trimethylsilyl-3,5-dichlorophenyl)-4H-azulenyl}) hafnium.

2,6-Dichloro-4-bromoaniline (15.6 g, 64.8 mmol) was gradually added to concentrated sulfuric acid (40 ml). The mixture was then stirred at room temperature for 20 minutes. The mixture was then cooled to 0° C. To the mixture was then added gradually sodium nitrite (4.9 g, 71.22 mmol). The mixture was then stirred at a temperature of 0° C. to 5° C. for 2.5 hours. The mixture thus obtained was then added to ice-water (200 g). To the mixture was then added an aqueous solution of potassium iodide (12.9 g, 77.76 mmol) at 5° C. The mixture was then allowed to stand at 5° C. for 15 minutes and at room temperature for 1 hour. The mixture was then extracted with diethyl ether. The extract was washed with an aqueous solution of sodium thiosulfate, and then dried over magnesium sulfate. The solvent was then distilled off. The crude product thus obtained was then extracted with hexane (200 ml). The solvent was then distilled off. As a result, a crude product was obtained in an amount of 18.62 g. The crude product was then recrystallized from ethanol (75 ml). As a result, 2,6-dichloro-4-bromoiodobenzene was obtained (14.8 g; yield: 65%).

$^1$H NMR (400 MHz, CDCl$_3$) δ7.51 (s, 2H).

The 2,6-Dichloro-4-bromoiodobenzene (4.48 g, 12.7 mmol) was dissolved in diethyl ether (50 ml). To the solution was then added dropwise a hexane solution of n-butyl lithium (1.56 M, 8.2 ml) at −78° C. At the same temperature, the mixture was then stirred for 1 hour. To the mixture was then added dropwise trimethylsilyl trifluoromethanesulfonate (3.2 ml, 16.5 mmol). The mixture was then stirred at −78° C. for 1 hour and at room temperature for 30 minutes. After the quenching of the reaction with water, the mixture was then extracted with ether. The resulting organic phase was then dried over magnesium sulfate. The solvent was then distilled off. The crude product thus obtained was then distilled under reduced pressure in a glass tube oven so that it was purified to obtain 3,5-dichloro-4-trimethylsilyl-bromobenzene (3.39 g; yield: 90%).

$^1$H NMR (400 MHz, CDCl$_3$) δ0.50 (s, 9H, Me$_3$Si), 7.41 (s, 2H, arom).

The 3,5-Dichloro-4-trimethylsilyl-bromobenzene (1.8 g, 6.06 mmol) was dissolved in a mixture of hexane (30 ml) and diisopropyl ether (3 ml). To the solution was then added dropwise a pentane solution of t-butyl lithium (1.47 M, 8.2 ml) at −40° C. The mixture was then stirred at −5° C. for 1 hour. To the mixture was then added 2-ethylazulene (898 mg, 5.76 mmol) at once. The mixture was then stirred at room temperature for 1.5 hours. To the mixture were then added tetrahydrofuran (15 ml) and N-methylimidazole (0.015 ml). To the mixture was then added dimethyl dichlorosilane (0.33 ml, 2.73 mmol) at 0° C. The mixture was then stirred at 5° C. for 1.5 hours and at room temperature for 30 minutes. Thereafter, to the mixture was added water so that it was subjected to separation. The resulting organic phase was then dried over magnesium sulfate. The solvent was then distilled off under reduced pressure. The crude product thus obtained was then purified through column chromatography (silica gel produced by Merck Ltd., Japan; n-hexane/methylenechloride) to obtain dimethylsilylenebis{2-ethyl-4-(4-trimethylsilyl-3,5-dichlorophenyl)-1,4-dihydroazulene} (1.46 g, yield: 66%) as a desired product.

The ligand thus obtained (1.46 g, 1.8 mmol) was then dissolved in diisopropyl ether (6 ml). To the solution was then added dropwise a hexane solution of n-butyl lithium (1.56 M, 2.3 ml) at 0° C. The mixture was then stirred at room temperature for 1 hour. To the mixture was then added toluene (40 ml). The solution was then cooled to −10° C. To the mixture was then added hafnium tetrachloride (570 mg, 1.8 mmol). Thereafter, the mixture was gradually heated to room temperature where it was then stirred for 5 hours. The solvent was then distilled off to obtain a crude product (2.09 g).

(b) Purification

The crude product thus obtained (2.09 g) was then extracted with hexane (50 ml). To the extract were then added hexane (15 ml) and dichloromethane (5 ml). The mixture was then irradiated with light with a high pressure mercury lamp (100 W) for 30 minutes. The solvent was then distilled off. The residue was then extracted with pentane (25 ml). The extract was then recrystallized from pentane to obtain a component containing a racemate of dichloro(1,1'-dimethylsilylene bis{2-ethyl-4-(4-trimethylsilyl-3,5-dichlorophenyl)-4H-azulenyl})hafnium as a pentane-soluble content (764 mg).

$^1$H NMR (400 MHz, CDCl$_3$) δ0.52 (s, 18H, TMS), 1.04 (s, 6H, SiMe$_2$), 1.09 (t, 6H, 2-CH2CH3), 2.5–2.6 (m, 2H, 2-CHHCH3), 2.7–2.8 (m, 2H, 2-CHHCH3), 5.00 (d, 2H, 4-H), 5.8–6.1 (m, 6H), 5.99 (s, 2H), 6.79 (d, J=6 Hz, 2H), 7.29 (s, 4H).

(2) Cocatalyst

As a cocatalyst there was used methyl aluminoxane ("MMAO", produced by Tosoh Akzo Co., Ltd.).

(3) Polymerization of Propylene

Methyl aluminoxane ("MMAO", produced by Tosoh Akzo Co., Ltd.; 2.0 mmol as calculated in terms of aluminum atom) was introduced into an autoclave equipped with stirring, the autoclave having an inner volume of 1 l. Separately, into a catalyst feeder with a rupture disc was introduced the component containing a racemate (2.0 mg) obtained at the step (1) which had been diluted with toluene. Thereafter, into the autoclave was introduced propylene (700 ml). The rupture disc was then cut at room temperature. The mixture was heated to 70° C. where it was then subjected to polymerization for 1 hour to obtain 43 g of a polypropylene. The complex activity was 2.2×10$^4$ g-polymer/g-complex·hr. The polypropylene showed Tm of 159.9° C. and MFR of 0.1.

EXAMPLE-2

(1) Metallocene Complex

Dichloro(1,1'-dimethylsilylenebis{2-ethyl-4-(4-trimethylsilyl-3,5-dichlorophenyl)-4H-azulenyl})hafnium synthesized at the step (1) of Example-1 was used.

(2) Cocatalyst 100 g of a commercially available granulating montmorillonite (Benclay SL, produced by MIZUSAWA INDUSTRIAL CHEMICALS, LTD.) was dispersed in 660 ml of an ion-exchanging water having 133 g of magnesium sulfate heptahydrate and 109 g of sulfuric acid dissolved therein. The dispersion was then heated to 100° C. in 2 hours. The dispersion was then kept at the same temperature for 2 hours. Thereafter, the dispersion was allowed to cool to room temperature in 1 hour. The resulting slurry was then filtered to recover a cake. To the cake was then added purified water (3 l) so that it was slurried again. The slurry was then filtered. This procedure was then performed twice. The cake thus recovered was then dried at 110° C. in a nitrogen atmosphere overnight. As a result, 80 g of a chemically-treated carrier was obtained. To 400 mg of the chemically-treated montmorillonite was then added 1.6 ml of a 0.5 mol/l toluene solution of trimethyl aluminum. The mixture was then stirred at room temperature for 1 hour. Thereafter, the product was washed with toluene to prepare a toluene slurry of montmorillonite (concentration: 33 mg/ml) which was then used as a cocatalyst.

(3) Polymerization of Propylene

Triisobutyl aluminum (produced by Tosoh Akzo Co., Ltd.; 0.15 mmol as calculated in terms of aluminum atom) was introduced into an autoclave equipped with stirring, the autoclave having an inner volume of 1 l. Separately, into a catalyst feeder with a rupture disc was introduced the component containing a racemate (3.0 mg) obtained at the step (1) which had been diluted with toluene. Into the autoclave were introduced the montmorillonite slurry (containing 25 mg of montmorillonite) obtained at the aforementioned step (2) and triisobutyl aluminum (0.015 mmol as calculated in terms of aluminum atom) as cocatalysts. These components were then allowed to come in contact with each other for 30 minutes. Thereafter, into the autoclave was introduced propylene (700 ml). The rupture disc was then cut at room temperature. The mixture was heated to 80° C. where it was then subjected to polymerization for 1 hour to obtain 71 g of a polypropylene. The complex activity was 2.4×10$^4$ g-PP/g-complex·hr. The catalytic activity was 1,420 g-PP/g-cat·hr. The polypropylene showed MFR of 0.44 and a melting point of 160.0° C.

EXAMPLE-3

(1) Metallocene Complex (a) Synthesis of dichloro(1,1'-silafluorenylbis{2-ethyl-4-(4-trimethylsilyl-3,5-dichlorophenyl)-4H-azulenyl})hafnium.

To a solution of 4-trimethylsilyl-3,5-dichlorophenyl bromide (2.98 g, 10 mmol) in a mixture of hexane (50 ml) and diisopropyl ether (10 ml) was added dropwise a pentane solution of t-butyl lithium (13.4 ml, 19.9 mmol, 1.48 M) at −70° C. The mixture was then stirred at −10° C. for 1 hour. To the mixture was then added 2-ethyl azulene (1.48 g, 9.5 mmol, 0.95 eq.). The mixture was heated to room temperature where it was then stirred for about 1 hour. To the mixture were then added tetrahydrofuran (20 ml) and N-methylimidazole (20 μl). The mixture was then cooled to 0° C. Subsequently, to the mixture was added a THF solution (5 ml) of silafluorenyl dichloride (1.18 g, 4.7 mmol, 0.47 eq.). The mixture was heated to room temperature where it was then stirred for 2 hours. Thereafter, to the mixture was added water to cause separation. The resulting organic phase was then dried over magnesium sulfate. The solvent was then distilled off under reduced pressure to obtain a crude product (4.72 g). The crude product thus obtained was then purified through silica gel column chromatography (Type 60N silica gel, produced by KANTO KAGAKU CO., LTD.; hexane:dichloromethane=10:1) to obtain pure silafluorenylbis(2-ethyl-4-(4-trimethylsilyl-3,5-dichlorophenyl)1,4-dihydroazulene) (1.73 g, 1.87 mmol; yield: 40%).

Subsequently, the ligand thus obtained was dissolved in diethyl ether (10 ml). To the solution was then added dropwise a hexane solution of n-butyl lithium (2.37 ml, 3.74 mmol, 1.58 M) at 0° C. The mixture was gradually heated to room temperature where it was then stirred for 2 hours. To the mixture was then added toluene (80 ml). The mixture was then cooled to −60° C. To the mixture was then added hafnium tetrachloride (599 mg, 1.87 mmol). The mixture was heated to room temperature in about 30 minutes. The mixture was further stirred for 30 minutes. The solvent was then distilled off. The residue was then twice extracted with diethyl ether (20 ml). As a result, the component containing lithium chloride was removed as an insoluble content. A crude product containing a racemate of the desired complex was obtained as a soluble content.

(b) Purification

The solvent was then distilled off. The residue was then washed with hexane (20 ml) three times and with diethyl ether (20 ml) three times to obtain substantially pure racemate of dichloro(1,1'-silafluorenylbis{2-ethyl-4-(4-trimethylsilyl-3,5-dichlorophenyl)-4H-azulenyl})hafnium (440 mg).

$^1$H NMR (400 MHz, CDCl$_3$) δ0.46 (s, 18H, TMS), 1.01 (t, 6H, 2-CH$_2$CH$_3$), 2.7–2.8 (m, 2H, 2-CHHCH$_3$), 3.0–3.1 (m, 2H, 2-CHHCH$_3$), 5.02 (d, 2H, 4-H), 5.8–6.2 (m, 6H), 6.15 (s, 2H), 7.17 (s, 4H, arom), 7.30 (d, 2H), 7.46 (t, 2H), 7.59 (t, 2H), 8.02 (d, 2H), 8.31 (d, 2H).

(2) Cocatalyst

Into a 5 l separable flask equipped with an stirring blade and a reflux condenser was charged 1,700 g of purified water. To the purified water was then added 500 g of a 98% sulfuric acid. To the mixture was then added 300 g of a commercially available granulating montmorillonite (Benclay SL, produced by MIZUSAWA INDUSTRIAL CHEMICALS, LTD. average particle diameter: 19.5 μm). The mixture was then stirred. Thereafter, the mixture was reacted at 90° C. for 2 hours. The resulting slurry was then cleaned in a device comprising an aspirator connected to a nutsche and a suction bottle. To the cake thus recovered was then added a solution of 325 g of lithium sulfate monohydrate in 900 ml of water. The mixture was then reacted at 90° C. for 2 hours. The slurry thus obtained was then cleaned to a pH value of more than 4 in the device comprising an aspirator connected to a nutsche and a suction bottle. The cake thus recovered was then dried at 120° C. overnight. As a result, 270 g of a chemically-treated product was obtained. To 516 mg of the chemically-treated montmorillonite was added 1.8 ml of a 0.72 mol/l toluene solution of triisopropyl aluminum. The mixture was then stirred at room temperature for 1 hour. Thereafter, the product was washed with toluene to prepare a toluene slurry of montmorillonite (concentration: 25 mg/ml) which was then used as a cocatalyst.

(3) Polymerization of Propylene

Triisobutyl aluminum (produced by Tosoh Akzo Co., Ltd.; 2.0 mmol as calculated in terms of aluminum atom) was introduced into an autoclave equipped with stirring, the autoclave having an inner volume of 3 l. Separately, into a catalyst feeder with a rupture disc was introduced the complex (1.41 mg, 1.5 mmol) obtained at the step (1) which had been diluted with toluene. Into the autoclave were introduced the montmorillonite slurry (containing 50 mg of montmorillonite) obtained at the aforementioned step (2) and triisobutyl aluminum (7.5 μmol as calculated in terms of aluminum atom) as cocatalysts and then these components were allowed to come in contact with each other for 30 minutes. Thereafter, into the autoclave were introduced propylene (1,500 ml) and hydrogen (90 ml). The catalyst was then introduced into the autoclave from the catalyst feeder at room temperature. The mixture was heated to 75° C. where it was then subjected to polymerization for one hour to obtain 125 g of a polypropylene. The complex activity was $7.0 \times 10^4$ g-PP/g-complex·hr. The catalytic activity was 2,500 g-PP/g-cat·hr. The polypropylene showed MFR of 8.3 and a melting point of 162.3° C.

EXAMPLE-4

(1) Metallocene Complex (a) Synthesis of dichloro(1,1'-silafluorenylbis{2-ethyl-4-(4-trimethylsilyl-3,5-dimethylphenyl)-4H-azulenyl})hafnium 2,6-Dimethyl-4-bromoiodobenzene (5.04 g, 16.2 mmol) was dissolved in diethyl ether (50 ml). To the solution was then added dropwise a hexane solution of n-butyl lithium (2.6 M, 6.5 ml) at −50° C. The mixture was then stirred at the same temperature for 45 minutes. To the mixture was then added dropwise trimethylsilyl trifluoromethanesulfonate (3.7 ml, 19.4 mmol). The mixture was then stirred at −30° C. for 30 minutes and at room temperature overnight. After the quenching of the reaction with water, the product was then extracted with diethyl ether. The resulting organic phase was then dried over magnesium sulfate. The solvent was then distilled off. The crude product thus obtained was then distilled under reduced pressure using a glass tube oven so that it was purified to obtain 3,5-dimethyl-4-trimethylsilylbromobenzene (3.54 g; yield: 85%).

$^1$H NMR (400 MHz, CDCl$_3$) δ0.39 (s, 9H, Me$_3$Si), 2.42 (s, 6H, Me$_2$), 7.13 (s, 2H, arom).

To a solution of the 3,5-dimethyl-4-trimethylsilyl-bromobenzene (1.91 g, 7.44 mmol) in a mixture of hexane (30 ml) and diisopropyl ether (15 ml) was added dropwise a pentane solution of t-butyl lithium (9.5 ml, 14.1 mmol, 1.49 M) at −40° C. The mixture was then stirred at −5° C. for 1 hour. To the mixture was then added 2-ethyl azulene (1.1 g, 7.07 mmol, 0.95 eq.). The mixture was heated to room temperature where it was then stirred for about 1 hour. To the mixture were then added tetrahydrofuran (20 ml). As a result, a homogeneous brown solution was obtained. To the solution was then added N-methylimidazole (30 μl). The mixture was then cooled to 5° C. Subsequently, to the mixture was added a THF solution (10 ml) of silafluorenyl dichloride (860 mg, 3.42 mmol, 0.46 eq.). The mixture was heated to room temperature where it was then stirred for 3 hours. Thereafter, to the mixture was added water to cause separation. The resulting organic phase was then dried over magnesium sulfate. The solvent was then distilled off under reduced pressure to obtain 3.15 g of a crude product.

(b) Purification

The crude product thus obtained was then purified through silica gel column chromatography (Type 60N silica gel, produced by KANTO KAGAKU CO., LTD. neutral, spherical, 63–210 μm, 30 g (column filled with silica gel which has swollen with hexane); hexane:dichloromethane=10:1) to obtain pure silafluorenylbis(2-ethyl-4-(4-trimethylsilyl-3,5-dimethylphenyl)1,4-dihydroazulene) (2.32 g; yield: 80%).

Subsequently, the ligand thus obtained was dissolved in diethyl ether (20 ml). To the solution was then added dropwise a hexane solution of n-butyl lithium (3.5 ml, 5.5 mmol, 1.57 M) at 0° C. The mixture was gradually heated to room temperature where it was then stirred for 2 hours. The solvent was then distilled off. To the residue were then added toluene (80 ml) and diethyl ether (8 ml). The mixture was then cooled to −35° C. To the mixture was then added hafnium tetrachloride (880 mg, 2.75 mmol). The mixture was then stirred at room temperature for 3.5 hours. The mixture was then subjected to decantation to remove inorganic products. The solvent was then distilled off. To the residue was then added pentane (15 ml). The insoluble content was then separated. The product was then washed with pentane (10 ml, 5 ml). As a result, a crude product containing a racemate of the desired complex was obtained (858 mg). The crude product was then washed with pentane (30 ml) twice to obtain a substantially pure racemate of dichloro(1,1'-silafluorenylbis{2-ethyl-4-(4-trimethylsilyl-3,5-dimethylphenyl)-4H-azulenyl})hafnium (605 mg).

$^1$H NMR. (400 MHz, CDCl$_3$) δ0.36 (s, 18H, TMS), 1.00 (t, 6H, 2-CH$_3$), 2.41 (s, 12H, Me$_2$), 2.7–3.1 (m, 4H, 2-CH$_2$CH$_3$), 5.05 (d, 2H, 4-H), 5.8–6.1 (m, 6H), 6.16 (s, 2H), 6.90 (s, 4H, arom), 6.92 (d, 2H), 7.47 (t, 2H), 7.60 (t, 2H), 8.03 (d, 2H), 8.35 (d, 2H).

(2) Cocatalyst

The montmorillonite slurry prepared at the step (2) of Example 3 (concentration: 50 mg) was used.

(3) Polymerization of Propylene

The procedure of Example 3 was followed except that 1.64 mg of the metallocene complex obtained at the aforementioned step (1) was used. As a result, 91 g of a polypropylene was obtained. The complex activity was 5.5×10$^4$ g-PP/g-complex·hr. The catalytic activity was 1,800 g-PP/g-cat·hr. The polypropylene showed a melting point of 161.7° C. and MFR of 2.4.

COMPARATIVE EXAMPLE-1

(The comparative example involves a transition metal complex without substituent in the 5-position of phenyl group.)

(1) Metallocene Complex (1) Synthesis of dichloro(1,1'-dimethylsilylenebis{2-ethyl-4-(3-chloro-4-trimethylsilylphenyl)-4H-azulenyl})hafnium.

3-chloro-4-iodobromobenzene (3.1 g) was dissolved in diethyl ether (100 ml). To the solution was then added dropwise a hexane solution of n-butyl lithium (1.59 M, 6.1 ml) at –78° C. The mixture was then stirred at the same temperature for 30 minutes. To the mixture was then added dropwise trimethylsilyl trifluoromethane sulfonate (3.77 ml; 17.4 mmol). The mixture was then stirred for 1 hour. After the quenching of the reaction by gradually adding water over an ice bath, the product was then extracted with ether. The resulting organic phase was then dried over magnesium sulfate. The solvent was then distilled off under reduced pressure. The crude product thus obtained was then purified twice through silica gel column chromatography (silica gel produced by Merck Ltd., Japan; hexane) to obtain 3-chloro-4-trimethylsilyl-bromobenzene (2.3 g) (yield: 90%).

$^1$H NMR (400 MHz, CDCl$_3$) δ0.35 (s, 9H, TMS), 7.3–7.4 (m, 2H, arom), 7.50 (s, 1H, arom).

To a solution of the 3-chloro-4-trimethylsilyl-bromobenzene (5 g) in a mixture of hexane (80 ml) and diisopropyl ether (20 ml) was added dropwise a pentane solution of t-butyl lithium (1.49M, 25.4 ml) at –78° C. The mixture was then stirred at –78° C. for 30 minutes. The mixture was then heated to 0° C. To the mixture was then added 2-ethyl azulene (2.8 g). The mixture was immediately heated to room temperature where it was then stirred for 1 hour. The suspension reaction solution was then allowed to stand to cause precipitation. The resulting supernatant liquid was then removed. To the residue was then added hexane. The mixture was stirred, and then allowed to stand to cause precipitation. This procedure was performed three times. To the mixture were then added tetrahydrofuran (40 ml), hexane (40 ml) and N-methylimidazole (0.02 ml). To the mixture was then added dropwise dimethylsilyl dichloride (1.08 ml) at –5° C. The mixture was then stirred at the same temperature for 1.5 hours. To the reaction solution was then added distilled water. The reaction solution was then extracted with diethyl ether. The resulting organic phase was then dried over magnesium sulfate. The solvent was then distilled off under reduced pressure to obtain 6.0 g of a crude product of dimethylsilylenebis{2-ethyl-4-(3-chloro-4-trimethylsilyl-phenyl)-1,4-dihydroazulene}.

(b) Purification

The ligand thus obtained (6 g) was dissolved in diisopropyl ether (30 ml). To the solution was then added dropwise a hexane solution of n-butyl lithium (1.58 M, 10.3 ml) at –2° C. The mixture was then stirred for 1.5 hours. To the mixture was then added toluene (180 ml). The mixture was then cooled to –78° C. To the mixture was then added hafnium tetrachloride (2.59 g). The mixture was gradually heated to room temperature where it was then stirred for 4 hours. The reaction solution thus obtained was concentrated, extracted with hexane, and then again concentrated to dryness. The product was repeatedly washed with n-pentane, washed with a 1:3 mixture of diethyl ether and hexane, and then extracted with methylene chloride. As a result, 0.47 g (yield: 6%) of a racemate of dichloro(1,1'-dimethylsilylenebis{2-ethyl-4-(3-chloro-4-trimethylsilylphenyl)-4H-azulenyl})hafnium was obtained as a desired product.

$^1$H NMR (400 MHz, CDCl$_3$) δ0.36 (s, 18H, TMS), 1.00 (s, 6H, SiMe$_2$), 1.05 (t, J=5.6 Hz, 6H, 2-CH$_2$CH$_3$), 2.5–2.7 (m, 4H, 2-CH$_2$CH$_3$), 5.00 (d, J=3.0 Hz, 2H, 4-H), 5.8–6.1 (m, 6H), 5.99 (s, 2H), 6.79 (d, J=6.0 Hz, 2H, 7-H), 7.2–7.4 (m, 6H, arom).

(2) Cocatalyst

The montmorillonite slurry prepared at the step (2) of Example 2 (concentration: 33 mg/ml) was used as a cocatalyst.

(3) Polymerization of Propylene

Triisobutyl aluminum (produced by Tosoh Akzo Co., Ltd.; 0.15 mmol as calculated in terms of aluminum atom) was introduced into an autoclave equipped with stirring, the autoclave having an inner volume of 1 l. Separately, into a catalyst feeder with a rupture disc was introduced the complex (0.7 mg) obtained at the step (1) which had been diluted with toluene. Into the autoclave were introduced the montmorillonite slurry (containing 25 mg of montmorillonite) obtained at the aforementioned step (2) and triisobutyl aluminum (0.015 mmol as calculated in terms of aluminum atom) as cocatalysts. These components were then allowed to come in contact with each other for 30 minutes. Thereafter, into the autoclave was introduced propylene (700 ml). The rupture disc was then cut at room temperature. The mixture was heated to 80° C. where it was then subjected to polymerization for 1 hour to obtain 17 g of a polypropylene. The complex activity was 2.4×10$^4$ g-PP/g-complex·hr. The catalytic activity was 690 g-PP/g-cat·hr. The polypropylene showed MFR of 0.27 and a melting point of 159.1° C.

COMPARATIVE EXAMPLE-2

As a compound analogue to the metallocene complex which is the subject of the present invention there is described in Example 2 of JP-A-2002-12596 a case where a propylene is polymerized in the presence of a metallocene catalyst made of a racemate of dichloro{1,1'-dimethylsilylenebis(2-ethyl-4-(4-trimethylsilylphenyl)-4H-azulenyl)}hafnium and a clay mineral. The complex further has substituents on the phenyl substituent on the azulenyl skeleton. However, these substituents are only trimethylsilyl groups. The polymer thus obtained has a melting point of 157.4° C., which is lower than those of Examples 1 to 4 of the present invention.

COMPARATIVE EXAMPLE-3

As a compound analogue to the metallocene complex which is the subject of the present invention there is also described in Example 3 of JP-A-11-189617 a case where a propylene is polymerized in the presence of a metallocene catalyst made of a racemate-meso mixture of 9-silafluorene-9,9-diylbis{1,1'-(2-methy-4-phenyl-4-hydroazulenyl)}zirconium dichloride and a clay mineral. The complex has an annular group which bridges two azulenyl ligands, but the phenyl group on the azulenyl skeleton is unsubstituted. The polymer thus obtained has a melting point of 147.9° C., which is far lower than those of Examples 1 to 4 of the present invention.

COMPARISON OF EXAMPLES WITH COMPARATIVE EXAMPLES

The comparison of the aforementioned examples and comparative examples shows that the examples of the present invention, which involve the use of a transition metal complex having substituents at the 3-, 4-and 5-position of phenyl group, in α-olefin polymerization using a clay catalyst as a cocatalyst, allow the substituents on the phenyl group to exert an enhanced catalytic effect of controlling the direction of growth of polymer chain and the direction of coordination of monomers, making it possible to produce a polymer having an enhanced stereoregularity and a increase of melting point, about 1° C. though, as compared with the comparative examples, which involve the use of a transition metal complex without substituents at the 5-position of phenyl group.

Further, the examples which involve the use of a transition metal complex having an annular bridging group Q show a further enhancement of melting point.

In the development of olefin polymerization catalyst complex, the production of polymers having a higher melting point has long been and will be a main subject. The difference in melting point of 1° C. is sufficiently significant. Even a melting temperature rise of 1° C. within a high melting temperature range can be a significant inventive step.

Further, the examples disclose that the catalyst thus obtained has a considerably excellent activity as compared with the comparative examples. It is made obvious that a polyolefin having a high molecular weight, a high melting point and excellent physical properties which can be extruded or injection-molded can be obtained in a high yield.

The present application claims foreign priority based on Japanese Patent Application No. JP2003-340108 filed Sep. 30 of 2003, the contents of which is incorporated herein by reference.

What is claimed is:

1. A catalyst component for olefin polymerization, comprising a transition metal compound represented by formula (I):

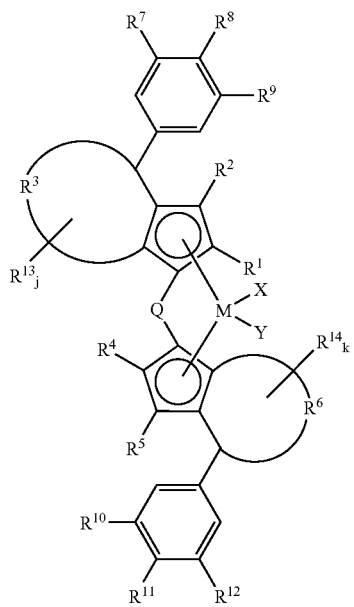

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3, or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, and $R^{13}$ and $R^{14}$ substitute a hydrogen atom in the hydrocarbon group represented by $R^3$ and $R^6$, respectively;

j and k each represent an integer of 0 to 8;

Q represents a bridging group connecting two cyclopentadienyl rings;

X and Y each represent an auxiliary ligand which is σ-covalently bound, the auxiliary ligand being-capable of reacting with a cocatalyst to develop an olefin-polymerizing capability; and M represents a transition metal belonging to the group IV in the periodic table.

2. The catalyst component for olefin polymerization according to claim 1, wherein the transition metal compound represented by formula (I) has an asymmetrical molecular structure about a plane including M, X and Y.

3. The catalyst component for olefin polymerization according to claim 1, wherein $R^8$ and $R^{11}$ each independently represent a silicon-containing hydrocarbon group having a carbon number of 3 to 10 or a branched aliphatic hydrocarbon group having a carbon number of 3 to 10.

4. The catalyst component for olefin polymerization according to claim 3, wherein $R^7$, $R^9$, $R^{10}$ and $R^{12}$ each area halogen atom.

5. The catalyst component for olefin polymerization according to claim 1, wherein the transition metal compound is represented by formula (II):

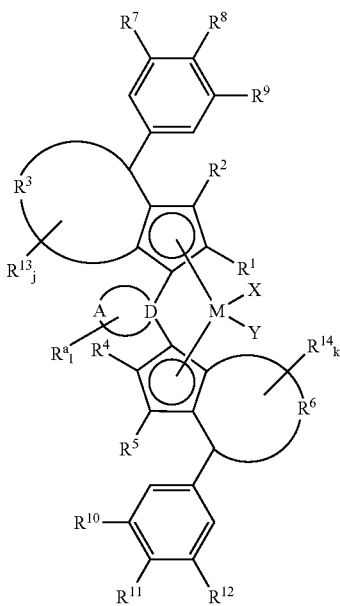

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3 or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, wherein $R^{13}$ substitutes a hydrogen atom in the hydrocarbon group represented by $R^3$, and $R^{14}$ substitutes a hydrogen atom in the hydrocarbon group represented by $R^6$;

j and k each represent an integer of from 0 to 8;

D represents a carbon atom, silicon atom, germanium atom or tin atom;

A represents a divalent saturated or unsaturated hydrocarbon group that has a carbon number of 3 to 5 and that forms a first ring with D;

$R^a$ represents a hydrocarbon group having a carbon number of 1 to 6 or a halogen-containing hydrocarbon group having a carbon number of 1 to 6, and $R^a$ is a substituent to be added to A, wherein a plurality of $R^a$'s may combine to form a second ring which is condensed to the first ring;

l represents an integer of 0 to 10;

X and Y each represent an auxiliary ligand which is σ-covalently bound, the auxiliary ligand being capable of reacting with a cocatalyst to develop an olefin-polymerizing capability; and M represents a transition metal belonging to the group IV in the periodic table.

6. A catalyst for α-olefin polymerization, which comprises:

(A) a transition metal compound represented by formula (I) according to claim 1; and (B) a component at least one of an aluminum oxy compound, an ionic compound capable of reacting with the transition metal compound to convert the transition metal compound to a cation, a Lewis acid, and a solid acid.

7. The catalyst for α-olefin polymerization according to claim 6, which further comprises (C) a particulate carrier.

8. A catalyst for α-olefin polymerization, which comprises:

(A) a transition metal compound represented by formula (I) according to claim 1; and (D) at least one of an ion-exchanging layered compound and an inorganic silicate.

9. The catalyst for α-olefin polymerization according to claim 8, which further comprises (E) an organic aluminum compound.

10. A process for producing an α-olefin polymer, which comprises bringing an α-olefin into contact with a catalyst according to claim 6 to polymerize or copolymerize the α-olefin.

11. A process for producing an α-olefin polymer, which comprises bringing an α-olefin into contact with a catalyst according to claim 8 to polymerize or copolymerize the α-olefin.

12. A transition metal compound represented by the formula (I):

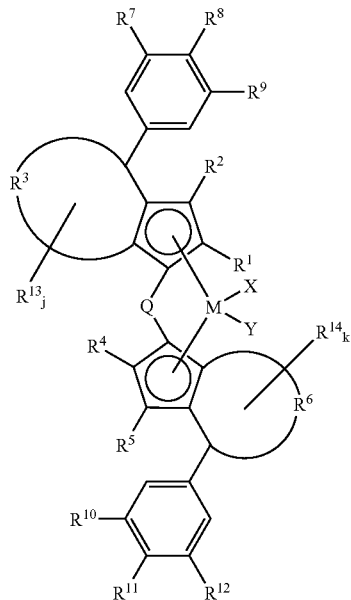

wherein $R^1$, $R^2$, $R^4$ and $R^5$ each independently represent a hydrogen atom, a hydrocarbon group having a carbon number of 1 to 6, a silicon-containing hydrocarbon group having a carbon number of 1 to 7 or a halogenated hydrocarbon group having a carbon number of 1 to 6;

$R^3$ and $R^6$ each represent a hydrocarbon group which is connected to the cyclopentadienyl ring to form any one of a 5- to 10-membered condensed ring;

$R^7$, $R^9$, $R^{10}$ and $R^{12}$ each independently represent a hydrocarbon group having a carbon number of 1 to 4, a halogenated hydrocarbon group having a carbon number of 1 to 3, or halogen atom;

$R^8$ and $R^{11}$ each independently represent a hydrocarbon group having a carbon number of 3 to 10 and the hydrocarbon group may contain a silicon atom, wherein a phenyl group and a substituted phenyl group are excluded from the hydrocarbon atom;

$R^{13}$ and $R^{14}$ each independently represent a hydrocarbon group having a carbon number of 1 to 20 or a halogenated hydrocarbon group having a carbon number of 1 to 20, and $R^{13}$ and $R^{14}$ substitute a hydrogen atom in the hydrocarbon group represented by $R^3$ and $R^6$, respectively;

j and k each represent an integer of 0 to 8;

Q represents a bridging group connecting two cyclopentadienyl rings;

X and Y each represent an auxiliary ligand which is σ-covalently bound to M; and M represents a transition metal belonging to the group IV in the periodic table.

* * * * *